United States Patent
Cho et al.

(10) Patent No.: US 10,765,359 B2
(45) Date of Patent: Sep. 8, 2020

(54) DEVICE-BASED DETECTION AND MONITORING OF SLEEP APNEA CONDITIONS

(71) Applicant: Medtronic, Inc., Minneapolis, MN (US)

(72) Inventors: Yong K. Cho, Excelsior, MN (US); Shantanu Sarkar, Roseville, MN (US); Eduardo N. Warman, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 248 days.

(21) Appl. No.: 15/381,815

(22) Filed: Dec. 16, 2016

(65) Prior Publication Data

US 2018/0168502 A1    Jun. 21, 2018

(51) Int. Cl.
  *A61B 5/042* (2006.01)
  *A61B 5/00* (2006.01)
  (Continued)

(52) U.S. Cl.
  CPC .......... *A61B 5/4818* (2013.01); *A61B 5/0452* (2013.01); *A61B 5/0456* (2013.01);
  (Continued)

(58) Field of Classification Search
  CPC .... A61B 5/0205; A61B 5/0816; A61B 5/4818
  See application file for complete search history.

(56) References Cited

U.S. PATENT DOCUMENTS

| | | |
|---|---|---|
| 5,117,824 A | 6/1992 | Keimel et al. |
| 5,485,851 A | 1/1996 | Erickson |

(Continued)

FOREIGN PATENT DOCUMENTS

| | | |
|---|---|---|
| EP | 0940155 B1 | 4/2004 |
| EP | 1583583 B1 | 3/2010 |

(Continued)

OTHER PUBLICATIONS

Guilleminault, C., et al., Cyclical Variation of the Heart Rate in Sleep Apnoea Syndrome. Lancet, 1984. 1(8369): p. 126-131.

(Continued)

*Primary Examiner* — Michael J D Abreu
(74) *Attorney, Agent, or Firm* — Shumaker & Sieffert, P.A.

(57) ABSTRACT

Sensing circuitry of an implantable medical device (IMD) system may sense a cardiac signal that varies according to a cardiac cycle of a patient. Processing circuitry of the IMD system may determine a series of consecutive cardiac cycle length metric values based on the sensed cardiac signal, identify a plurality of pairs of the cardiac cycle length metrics, each of the pairs of cardiac cycle length metrics separated by an integer 'n' of the cardiac cycle length metrics, and construct a distribution of the pairs of cardiac cycle length metrics based on values of the cardiac cycle length metrics for each of the pairs. The processing circuitry may detect a sleep apnea episode of the patient based on one or more characteristics of the constructed distribution, and control communication circuitry of the IMD system to transmit an indication of the detected sleep apnea episode to the external computing device.

20 Claims, 14 Drawing Sheets

(51) Int. Cl.
*A61B 5/0456* (2006.01)
*A61B 5/0452* (2006.01)
*A61N 1/39* (2006.01)
*A61N 1/37* (2006.01)
*A61B 5/07* (2006.01)

(52) U.S. Cl.
CPC ............ *A61B 5/686* (2013.01); *A61B 5/7282* (2013.01); *A61B 5/746* (2013.01); *A61B 5/0031* (2013.01); *A61B 5/0422* (2013.01); *A61B 5/07* (2013.01); *A61B 5/4836* (2013.01); *A61N 1/3702* (2013.01); *A61N 1/3925* (2013.01); *A61N 1/3956* (2013.01)

(56) References Cited

U.S. PATENT DOCUMENTS

| | | | |
|---|---|---|---|
| 6,881,192 | B1 | 4/2005 | Park |
| 6,999,817 | B2 | 2/2006 | Park et al. |
| 7,031,765 | B2 | 4/2006 | Ritscher et al. |
| 7,160,252 | B2 | 1/2007 | Cho et al. |
| 7,212,862 | B2 | 5/2007 | Park et al. |
| 7,225,021 | B1 | 5/2007 | Park et al. |
| 7,532,934 | B2 | 5/2009 | Lee et al. |
| 7,613,507 | B2 | 11/2009 | Vitali et al. |
| 7,623,911 | B2 | 11/2009 | Sarkar et al. |
| 7,725,181 | B1 | 5/2010 | Bomzin et al. |
| 7,819,816 | B2 | 10/2010 | Pu et al. |
| 7,831,303 | B2 | 11/2010 | Rueter et al. |
| 8,019,407 | B2 | 9/2011 | Lian et al. |
| 8,249,686 | B2 | 8/2012 | Libbus et al. |
| 8,437,851 | B2 | 5/2013 | Corbucci et al. |
| 8,579,824 | B2 | 11/2013 | Cho et al. |
| 8,915,741 | B2 | 12/2014 | Hatlestad et al. |
| 8,956,295 | B2 | 2/2015 | Ni et al. |
| 9,538,922 | B2 | 1/2017 | Wang |
| 2004/0134496 | A1* | 7/2004 | Cho ................ A61B 5/0205 128/204.23 |
| 2004/0138719 | A1 | 7/2004 | Cho et al. |
| 2005/0090871 | A1 | 4/2005 | Cho et al. |
| 2005/0119711 | A1 | 6/2005 | Cho et al. |
| 2007/0118180 | A1 | 5/2007 | Ni et al. |
| 2011/0105921 | A1* | 5/2011 | Wang ................ A61B 5/024 600/508 |
| 2012/0101541 | A1 | 4/2012 | Corbucci et al. |
| 2013/0165989 | A1 | 6/2013 | Gelfand et al. |
| 2015/0164349 | A1* | 6/2015 | Gopalakrishnan ................ A61B 5/02405 600/508 |

FOREIGN PATENT DOCUMENTS

| | | |
|---|---|---|
| EP | 2179690 A1 | 4/2010 |
| WO | 03086531 A2 | 10/2003 |
| WO | 2008094816 A2 | 8/2008 |
| WO | 2015089484 A1 | 6/2015 |

OTHER PUBLICATIONS

Penzel et al., "MESAM: A heart rate and snoring recorder for detection of obstructive sleep apnea." Sleep, Published Oct. 1989, 13(2): p. 175-182.
International Search Report and Written Opinion of International Application No. PCT/US2017/065556, dated Apr. 4, 2018, 14 pp.
Aljadeff et al., "Heart Rate Variability in Children With Obstructive Sleep Apnea," Sleep, vol. 20, No. 2, Feb. 1, 1997, pp. 151-157.
Zhang et al., "Obstructive Sleep Apnoea and Atrial Fibrillation," Arrhythmia & Electrophysiology Review 2015, Jan. 2015, pp. 14-18.
Esperer et al., "Cardiac Arrhythmias Imprint Specific Signatures on Lorenz Plots," Annals of Noninvasive Electrocardiology, vol. 13, No. 1, Jan. 2008, pp. 44-60.
International Preliminary Report on Patentability from International Application No. PCT/US2017/065556, dated Jun. 18, 2019, 9 pp.
Communication Pursuant to Rules 161(1) and 162 EPC dated Jul. 26, 2019 from counterpart European Application No. 17823292.2, 3 pp.
Response to Communication Pursuant to Rules 161(1) and 162 EPC dated Jul. 26, 2019 from counterpart European Application No. 17823292.2, Filed Feb. 5, 2020, 6 pp.

* cited by examiner

DEVICE-BASED DETECTION AND MONITORING OF SLEEP APNEA CONDITIONS

TECHNICAL FIELD

This disclosure relates to medical devices and, more particularly, to medical devices that monitor physiological conditions of a patient.

BACKGROUND

When functioning properly, a heart maintains its own intrinsic rhythm, and is capable of pumping adequate blood throughout a circulatory system. This intrinsic rhythm is a function of intrinsic signals generated by the sinoatrial node, or SA node, located in the upper right atrium. The SA node periodically depolarizes, which in turn causes the atrial heart tissue to depolarize such that right and left atria contract as the depolarization travels through the atrial heart tissue. The atrial depolarization signal is also received by the atrioventricular node, or AV node, which, in turn, triggers a subsequent ventricular depolarization signal that travels through and depolarizes the ventricular heart tissue causing the right and left ventricles to contract.

Some patients, however, have irregular cardiac rhythms, referred to as cardiac arrhythmias. Cardiac arrhythmias result in diminished blood circulation because of diminished cardiac output. Atrial fibrillation is a common cardiac arrhythmia that reduces the pumping efficiency of the heart. Atrial fibrillation is characterized by rapid, irregular, uncoordinated depolarizations of the atria.

In addition to atrial fibrillation, a condition known as 'sleep apnea' can also diminish cardiac output and pose various risks to patients, particularly those who are susceptible to heart failure. Sleep apnea is a sleep disorder that involves the temporary cessation of respiratory airflow during sleep. In various scenarios, sleep apnea may be characterized by one or both of pauses in breathing or periods of shallow breathing during sleep.

Sleep apnea is generally considered a medical syndrome that occurs in various forms. One recognized form of sleep apnea is "central sleep apnea," which is associated with a failure of the central nervous system to automatically initiate and control respiration. Another recognized form of sleep apnea is "obstructive sleep apnea," which is associated with an obstruction of the airways due to airway collapse. Yet another recognized form of sleep apnea is a mixed form that may include a central nervous system failure to drive ventilatory effort combined with an obstructive apnea.

Possible effects of sleep apnea include daytime sleepiness, impaired alertness, and various associated cardiovascular diseases, which in turn can significantly impair patient lifestyle and increase morbidity risk. In some cases, obstructive sleep apnea can lead to death, due to lack of oxygen to vital organs of the body. Various approaches have been taken to detect and treat sleep apnea.

SUMMARY

Some existing monitoring systems have relied on respiratory measurement data to detect an episode of sleep apnea. Other examples of existing monitoring technology have relied on pulse oximetry, thoracic impedance, airway pressure, and various other measurements and metrics. These systems often require dedicated system infrastructure, such as a continuous positive airway pressure (CPAP) therapy system, or systems designed to implement thoracic impedance plethysmography (TIP). However, CPAP and TIP systems are often designed and manufactured for the exclusive purpose of sleep apnea, and thus, CPAP and TIP-based monitoring systems do not leverage hardware infrastructure that may also be used to monitor biological systems other than the respiratory system.

In one example, the disclosure provides a method of detecting sleep apnea by an implantable medical device (IMD) system. The method may include sensing, by sensing circuitry of the IMD system, a cardiac signal that varies as a function of a cardiac cycle of a patient, determining, by processing circuitry of the IMD system, a series of consecutive cardiac cycle length metric values based on the sensed cardiac signal, and identifying, by the processing circuitry of the IMD system, a plurality of pairs of the cardiac cycle length metrics, each of the pairs of cardiac cycle length metrics separated by an integer 'n' of the cardiac cycle length metrics. The method may further include constructing, by the processing circuitry of the IMD system, a distribution of the pairs of cardiac cycle length metrics based on values of the cardiac cycle length metrics for each of the pairs, detecting, by the processing circuitry of the IMD system, a sleep apnea episode of the patient based on one or more characteristics of the constructed distribution, and controlling, by the processing circuitry of the IMD system, communication circuitry of the IMD system to transmit an indication of the detected sleep apnea episode to the external computing device.

In another example, the disclosure provides a system including an implantable medical device (IMD). The IMD system may include communication circuitry configured to communicate with an external computing device, sensing circuitry configured to sense a cardiac signal that varies as a function of a cardiac cycle of a patient, and processing circuitry. The processing circuitry may be configured to determine a series of consecutive cardiac cycle length metric values based on the sensed cardiac signal, to identify a plurality of pairs of the cardiac cycle length metrics, each of the pairs of cardiac cycle length metrics separated by an integer 'n' of the cardiac cycle length metrics, and to construct a distribution of the pairs of cardiac cycle length metrics based on values of the cardiac cycle length metrics for each of the pairs. The processing circuitry may be further configured to detect a sleep apnea episode of the patient based on one or more characteristics of the constructed distribution, and to control the communication circuitry to transmit an indication of the detected sleep apnea episode to the external computing device.

In another example, the disclosure provides a system including means for sensing a cardiac signal that varies as a function of a cardiac cycle of a patient, means for determining a series of consecutive cardiac cycle length metric values based on the sensed cardiac signal, means for identifying a plurality of pairs of the cardiac cycle length metrics, each of the pairs of cardiac cycle length metrics separated by an integer 'n' of the cardiac cycle length metrics; means for constructing a distribution of the pairs of cardiac cycle length metrics based on values of the cardiac cycle length metrics for each of the pairs; and means for detecting a sleep apnea episode of the patient based on one or more characteristics of the constructed distribution, and means for generating an indication of the detected sleep apnea episode to the external computing device.

In another example, the disclosure provides a non-transitory computer-readable storage medium encoded with instructions. The instructions, when executed, cause processing circuitry of a medical device system to sense a cardiac signal that varies as a function of a cardiac cycle of a patient, determine a series of consecutive cardiac cycle length metric values based on the sensed cardiac signal, to identify a plurality of pairs of the cardiac cycle length metrics, each of the pairs of cardiac cycle length metrics separated by an integer 'n' of the cardiac cycle length metrics, to construct a distribution of the pairs of cardiac cycle length metrics based on values of the cardiac cycle length metrics for each of the pairs, and to detect a sleep apnea episode of the patient based on one or more characteristics of the constructed distribution; and to generate an indication of the detected sleep apnea episode to the external computing device.

In general, this disclosure is directed to systems configured to detect individual episodes of sleep apnea using one or more devices used to monitor a patient's heart function. Systems described herein may be configured to identify an individual episode of sleep apnea using data derived from a monitored heart rate. In various implementations, a system of this disclosure may be configured to analyze comparative data constructed using cardiac cycle length metrics in order to detect a sleep apnea episode. For instance, a medical device system configured according to aspects of this disclosure may collect data using an implantable medical device (IMD) to form discrete pairs of cardiac cycle length metrics, based on a fixed time interval between the two metrics of each respective pair. In some examples, the system of this disclosure may use a subcutaneous IMD to collect the data. In turn, the system may analyze a distribution of the pairs, based on the particular values indicated in the pairs of the cardiac cycle length metrics. A variety of the techniques described herein may be used independently, or in any combination, to detect sleep apnea episodes using the pairs of cardiac cycle metrics.

According to some aspects of this disclosure, the system utilizes a Lorenz plot of changes in R-wave intervals, i.e., R-R intervals, during the cardiac rhythm to detect a sleep apnea episode, using the degree of variability of cardiac cycle lengths. R-R intervals may be used as one method for determining the cardiac cycle length of each patient heartbeat. For instance, the system of this disclosure may pair R-R intervals that are separated by a predetermined number of the intervals, such as by 1 interval or by 10 intervals. In turn, the system may analyze a Lorenz plot that plots each R-R interval pair, to determine a level of dispersion (also referred to "dispersedness" or "directional scatter") of the data points. For instance, the system may implement the techniques of this disclosure to determine that a more dispersed Lorenz plot of the R-R interval pairs tends to indicate a sleep apnea episode, while a less dispersed (or "tighter") Lorenz plot tends to indicate an episode of respiratory sinus arrhythmia (RSA), and an even less dispersed Lorenz plot tends to indicate normal breathing.

Systems configured according to the aspects of this disclosure may provide one or more advantages over existing systems. For instance, the system uses cardiac measurements to detect sleep apnea episodes, thereby providing a more efficient mechanism than systems that rely on respiratory measurements to detect sleep apnea. Moreover, the system may leverage existing IMD infrastructure that is used for monitoring cardiac health, in order to also detect sleep apnea. Additionally, the systems of this disclosure are capable of relying on subcutaneous IMDs for measuring the R-R intervals, thereby using relatively less invasive implants.

The details of one or more examples of this disclosure are set forth in the accompanying drawings and in the description below. Other features, objects, and advantages will be apparent from the description and drawings, and from the claims.

DETAILED DESCRIPTION

Figure 1:
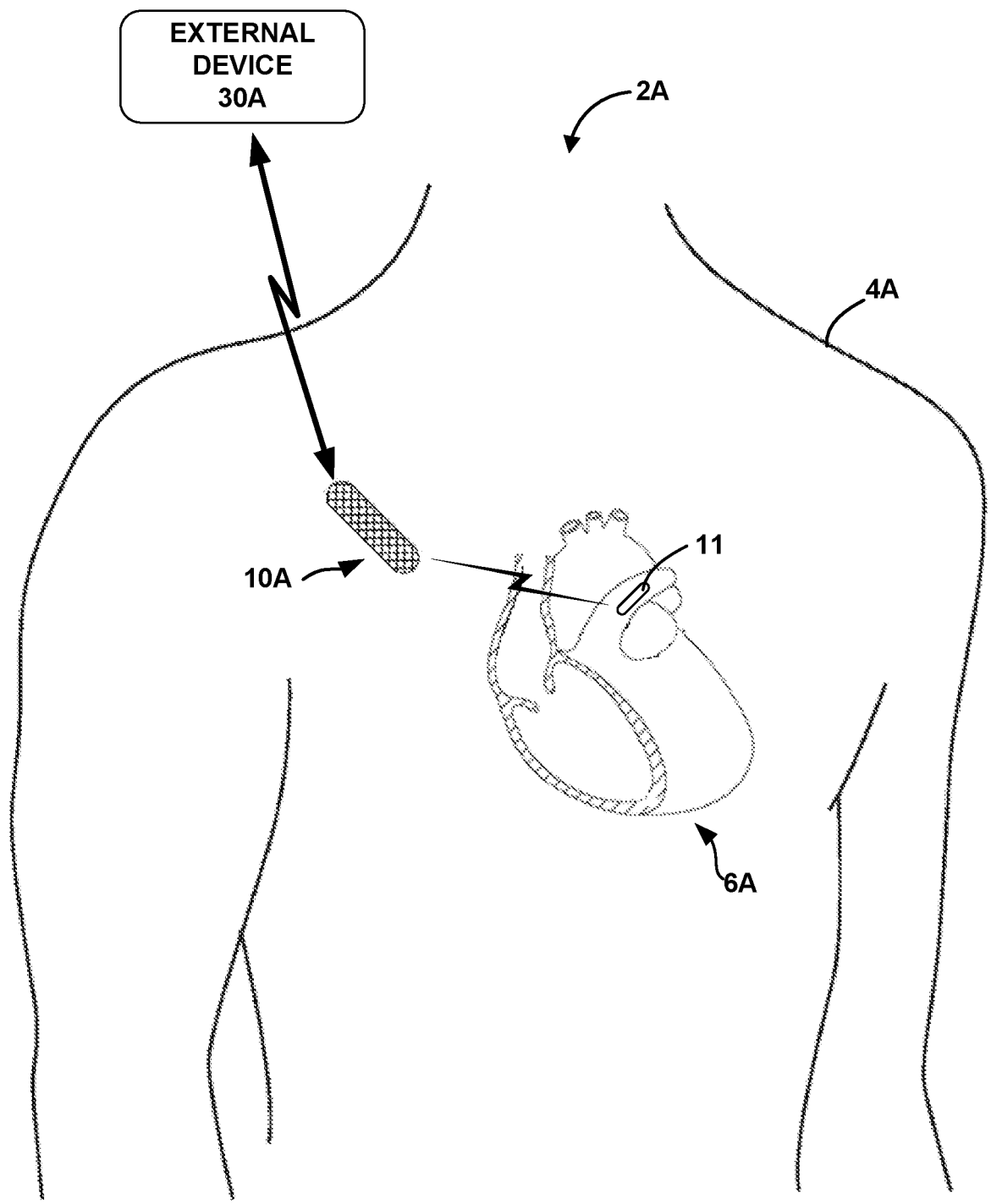
FIG. 1 is a conceptual diagram illustrating an example medical device system in conjunction with a patient, where the medical device system is configured to implement various sleep apnea detection and communication functionalities of this disclosure.

In general, this disclosure is directed to detecting individual episodes of sleep apnea. Sleep apnea is a breathing disorder that cuts oxygen supply to various systems and organs of the body. To deal with the reduction in oxygenation levels, organs and systems of the body may trigger one or more compensatory mechanisms. With respect to the cardiovascular system, the compensatory mechanism(s) cause the heart to increase blood output for a period of time. As such, the cardiac compensatory mechanisms cause increased exertion of the heart. Moreover, at the end of a sleep apnea event and during a recovery period that follows a sleep apnea episode, the patient's heart rate may increase significantly, due to alveolar hyperventilation caused by the pulmonary system's compensatory mechanisms. The heart rate spike after a sleep apnea episode may be greater in magnitude than naturally-occurring heart rate increases that are exhibited by the normal phenomenon of cyclical variation of heart rate (CVHR). As such, both the reduced oxygen supply during a sleep apnea episode and the hyperventilation that follows a sleep apnea episode may cause exertion levels in the heart that exceed normal levels of heart exertion.

The abnormal oxygenation conditions associated with sleep apnea may affect various systems and vital organs adversely. Repeated instances of increased heart exertion, as may be caused by frequent compensatory blood output to counter chronic sleep apnea and by increasing the heart rate to accommodate subsequent hyperventilation, increases the likelihood of heart ailments or possible heart failure. Techniques of this disclosure enable a medical monitoring system or therapy delivery system to leverage heart-related data collections to detect, and potentially counter, individual episodes of sleep apnea. The techniques described herein potentially provide a significantly lower-complexity and cost-efficient detection system than technologies that rely on using respiratory measurements to detect sleep apnea episodes. In some examples, various techniques described herein may be implemented in conjunction with respiratory measurement-based techniques to improve detection accuracy or to estimate/quantify the severity of the episode. For example, detection of a pause in respiration with a heart rate compensation following or with the respiration pause without heart rate compensation may indicate a greater likelihood of a sleep apnea episode. Further, the techniques of this disclosure may be combined this with pulse oxygenation levels to confirm changes in oxygen in blood. Other (e.g., more battery intensive) techniques can be triggered by the RR interval-based methods for confirmation of a sleep apnea episode.

The systems described herein may be configured to analyze pairs of cardiac cycle lengths, e.g., "R-R intervals" or "RRIs", to detect various types of cardiac arrhythmias, including sleep apnea. For instance, different distribution patterns of RRI pairs may be indicative of different conditions, such as normal breathing, respiratory sinus arrhythmia, or of sleep apnea. In various implementations, the systems described herein may analyze RRI pairs that are arranged using Lorenz plots. In other implementations, the systems described herein may analyze crests and troughs of RRI values plotted against the times at which they occur. In any case, the systems of this disclosure are configured to use RRI information to detect individual episodes of sleep apnea, and optionally, to trigger an alert and/or to trigger the delivery of therapy or medication of a delivered therapy.

FIG. 1 is a conceptual diagram illustrating an example medical device system 2A in conjunction with a patient 4A. Medical device system 2A is an example of a medical device system configured to implement the techniques described herein for detecting individual events of sleep apnea, and optionally, for responsively providing an alert indicating that the sleep apnea event is predicted. In the illustrated example, medical device system 2A includes an ICM 10A and an external device 30A. ICM 10A represents one example implementation of implantable medical device (IMD) 10 illustrated in FIG. 4, and described in further detail below.

ICM 10A is an insertable cardiac monitor (ICM) capable of sensing and recording cardiac EGM signals from a position outside of heart 6A, and will be referred to as ICM 10A hereafter. In some examples, ICM 10A includes or is coupled to one or more additional sensors that generate one or more other physiological signals, such as signals that vary based on patient motion and/or posture, heart motion and/or sounds, blood pressure, blood flow, blood oxygenation, or respiration. ICM 10A may be implanted outside of the thorax of patient 4A, e.g., subcutaneously or submuscularly, such as the pectoral location illustrated in FIG. 1. In some examples, ICM 10A may take the form of a Reveal LINQ™ ICM, available from Medtronic plc, of Dublin, Ireland.

External device 30A may be a computing device, e.g., used in a home, ambulatory, clinic, or hospital setting, to communicate with ICM 10A via wireless telemetry. External device 30A may be coupled to a remote patient monitoring system, such as Carelink®, available from Medtronic plc, of Dublin, Ireland. External device 30A may be, as examples, a programmer, external monitor, or consumer device, e.g., smart phone. External device 30A may be used to program commands or operating parameters into ICM 10A for controlling its functioning, e.g., when configured as a programmer for ICM 10A. External device 30A may be used to interrogate ICM 10A to retrieve data, including device operational data as well as physiological data accumulated in IMD memory. The interrogation may be automatic, e.g., according to a schedule, or in response to a remote or local user command. Programmers, external monitors, and consumer devices are examples of external devices 30A that may be used to interrogate ICM 10A. Examples of communication techniques used by ICM 10A and external device 30A include tissue conductance communication (TCC), or radiofrequency (RF) telemetry, which may be an RF link established via Bluetooth®, WiFi®, or medical implant communication service (MICS). Medical device system 2A also includes implantable pressure sensing device 11, also referred to as sensor device 11. For purposes of this description, knowledge of cardiovascular anatomy is presumed and details are omitted except to the extent necessary or desirable to explain the context of the techniques of this disclosure.

External device 30A may wirelessly communicate with ICM 10A, e.g., to program the functionality of the ICM, and to retrieve recorded physiological signals and/or patient parameter values or other data derived from such signals from the ICM. Both ICM 10A and external device 30A include processing circuitry, and the processing circuitry of either device or of both devices may perform the techniques described herein, such as determining patient parameter values for a period, determining difference metrics based on the patient parameter values, analyzing distribution of the difference metrics, and determining whether the distribution is indicative of a sleep apnea event or episode.

Based on the analysis of the cardiac cycle length distribution information, the processing circuitry of one or more of the devices may also be configured to provide an alert to a user, e.g., to a clinician and/or to patient 4A, that a likely sleep apnea event has been detected, e.g., via external device 30A. Although ICM 10A is not described as being configured to deliver therapy, patient 4A, a clinician, or another implanted or external medical device may deliver or take a preventative measure to prevent the occurrence of additional sleep apnea events.

ICM 10A may monitor a physiological parameter indicative of patient state, such as posture, heart rate, activity level, heart rate, and/or respiration rate, fluid/heart failure status (e.g., using impedance), and ICM 10A may measure the physiological parameter(s) at times when sensor device 11 is measuring cardiovascular pressure. Sensor device 11 may be implanted, as one example, within a pulmonary artery of patient 4A and may include pressure sensing circuitry configured to measure the cardiovascular pressure of patient 4A. In some examples, sensor device 11 may be a part of sensor assembly 10A. Each of sensor device 11 and ICM 10A may include a timer and processing circuitry configured to determine a time of day based on the timer value. If sensor device 11 determines that the current time is within a predetermined window that may be stored in memory of sensor device 11, sensor device 11 may measure and transmit the cardiovascular pressure of patient 4A to ICM 10A.

In some examples, sensor device 11 may include wireless communication circuitry configured to receive a trigger signal from ICM 10A. The pressure sensing circuitry of sensor device 11 may be configured to measure the cardiovascular pressure of patient 4A in response to receiving the trigger signal. In this manner, ICM 10A may dictate the times at which sensor device 11 measures cardiovascular pressure, and sensor device 11 may enter a low-power mode such as sleep mode until the wireless communication circuitry of sensor device 11 receives a trigger signal. ICM 10A may transmit posture data, and other physiological parameter data acquired by ICM 10A, to external device 30A. ICM 10A may also transmit cardiovascular pressure measurements received from sensor device 11 to external device 30A.

Although not illustrated in the example of FIG. 1, a medical device system configured to implement the techniques of this disclosure may include one or more implanted or external medical devices in addition to or instead of ICM 10A. For example, a medical device system may include a vascular ICD, an extravascular ICD, a cardiac pacemaker implanted outside of the heart 6A but coupled to intracardiac or epicardial leads, or an intracardiac pacing device. One or more such devices may generate physiological signals, and include processing circuitry configured to perform, in whole or in part, the techniques described herein for detecting sleep apnea. The implanted devices may communicate with each other and/or an external device 30A, and one of the implanted or external devices may ultimately determine whether sleep apnea is detected based on information received from the other device(s).

In various examples, IMD components may be connected to leads that extend into heart 6A, or could be implanted in heart 6A entirely. In some examples, components of medical device system 2A may be external devices. In any event, components of medical device system 2A may be configured to detect cardiac electrogram signals, such as an ECG. In various examples, processing circuitry of medical device system 2A, such as processing circuitry of ICM 10A and/or external device 30A, may perform the sleep apnea detection techniques of this disclosure using various types of sensing circuitry, such as sensing circuitry of ICM 10A and/or sensing circuitry of sensor 11 capable of detecting timing of cardiac depolarization or contraction. As such, aspects of medical device system 2 may detect sleep apnea episodes using various types of measurements, including cardiac cycle metrics sensed by ICM 10A and/or pressure-based readings sensed by sensor device 11.

Figure 2:
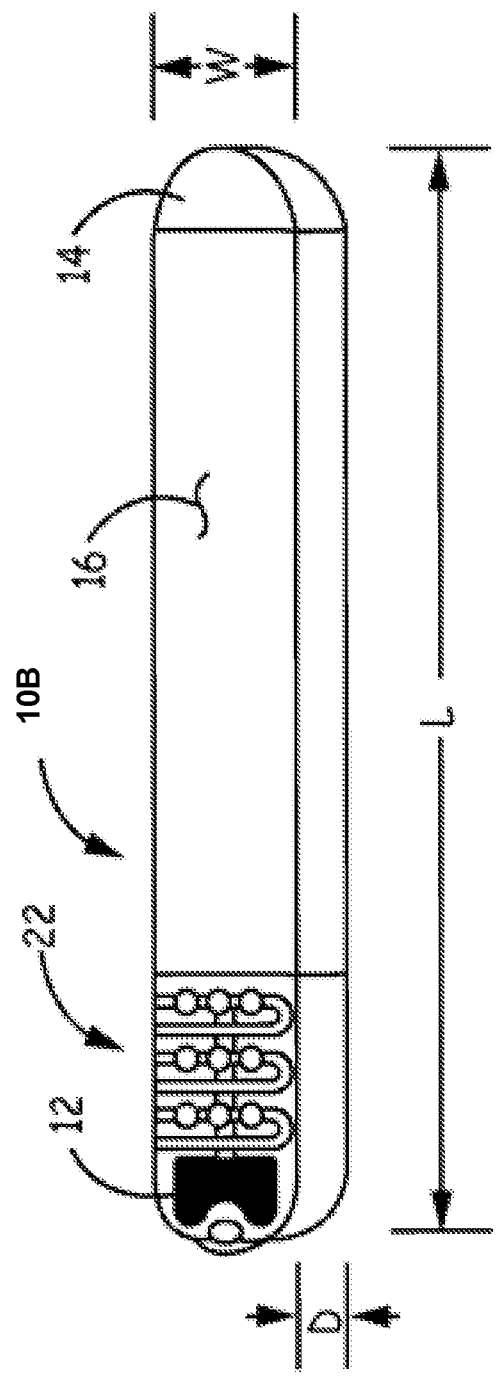
FIG. 2 is a perspective view of an example implantable cardiac monitor (ICM) configured to sense and record cardiac electrogram signals of a patient.

FIG. 2 is a perspective view of an example ICM 10B. ICM 10B of FIG. 2 represents an example implementation of ICM 10A illustrated in FIG. 1 and described above. ICM 10B also represents an example implementation of implantable medical device (IMD) 10 illustrated in FIG. 4, and described in further detail below. FIG. 2 shows ICM 10B in greater detail. From the view illustrated in FIG. 2, it can be seen that ICM 10B includes two electrodes, namely, electrodes 12 and 14. Electrodes 12 and 14 are positioned adjacent the proximal and distal ends, respectively, of ICM 10B. When implanted, electrode 12, located on the upper surface 16 of ICM 10B may face outward, e.g., toward the skin of patient 4A. As such, when ICM 10B is placed into a handle, the electrode 12 faces downward and is not visible through the open upper portion of the channel, allowing verification of proper insertion into the handle.

As shown in the view illustrated in FIG. 2, ICM 10B generally takes the form of an elongated rectangular prism having rounded corners and a rounded distal end portion. The rounded distal end of ICM 10B is conducive in terms of allowing ICM 10B to advance into body tissue. More specifically, the rounded distal end portion of ICM 10B enables blunt dissection of the tissue as ICM 10B advances through the tissue. Because the cross section of ICM 10B is substantially greater in area than the cross section area of a corresponding tunneler, ICM 10B may be positioned snugly within the body tissue, reducing the chances for the formation of air bubbles adjacent to the electrodes and also assisting in maintaining the device in its desired position. ICM 10B has a length denoted by 'L,' a width denoted by 'W,' and a depth denoted by 'D' as illustrated in FIG. 2.

Although FIG. 2 is not necessarily drawn to scale, in the example of FIG. 2, the width of ICM 10B is greater than the depth of ICM 10B, thereby providing radial asymmetry along the longitudinal axis of ICM 10B. Moreover, the dimensionality of ICM 10B may assist in maintaining ICM 10B in its proper orientation, with upper surface 16 facing outward after implant into the body of patient 4A. A suture hole may optionally be provided at the proximal end of ICM 10B to enable a physician to suture ICM 10B to underlying tissue if desired. Projections 22 may optionally be provided to prevent longitudinal movement of the device after implant.

Components of ICM 10B, functioning individually or in various combinations, may be operable to sense cardiac cycle information with respect to patient 4A, express the sensed data in a format interpretable by humans and/or other devices, and communicate the data. For instance, ICM 10B may communicate RRI information, sensed from a pulse exhibited by patient 4A, to external device 30A. In various use case scenarios, a physician or clinician may implant ICM 10B subcutaneously in the body of patient 4A, in order to gather RRI information that can be used for monitoring cardiac function and/or, according to aspects of this disclosure, pulmonary function. For instance, the RRI data gathered by ICM 10B may be analyzed by external device 30A to detect likely episodes of sleep apnea on an episode-by-episode basis, and optionally, to generate an alert indicating that therapy may be required.

Figure 3:
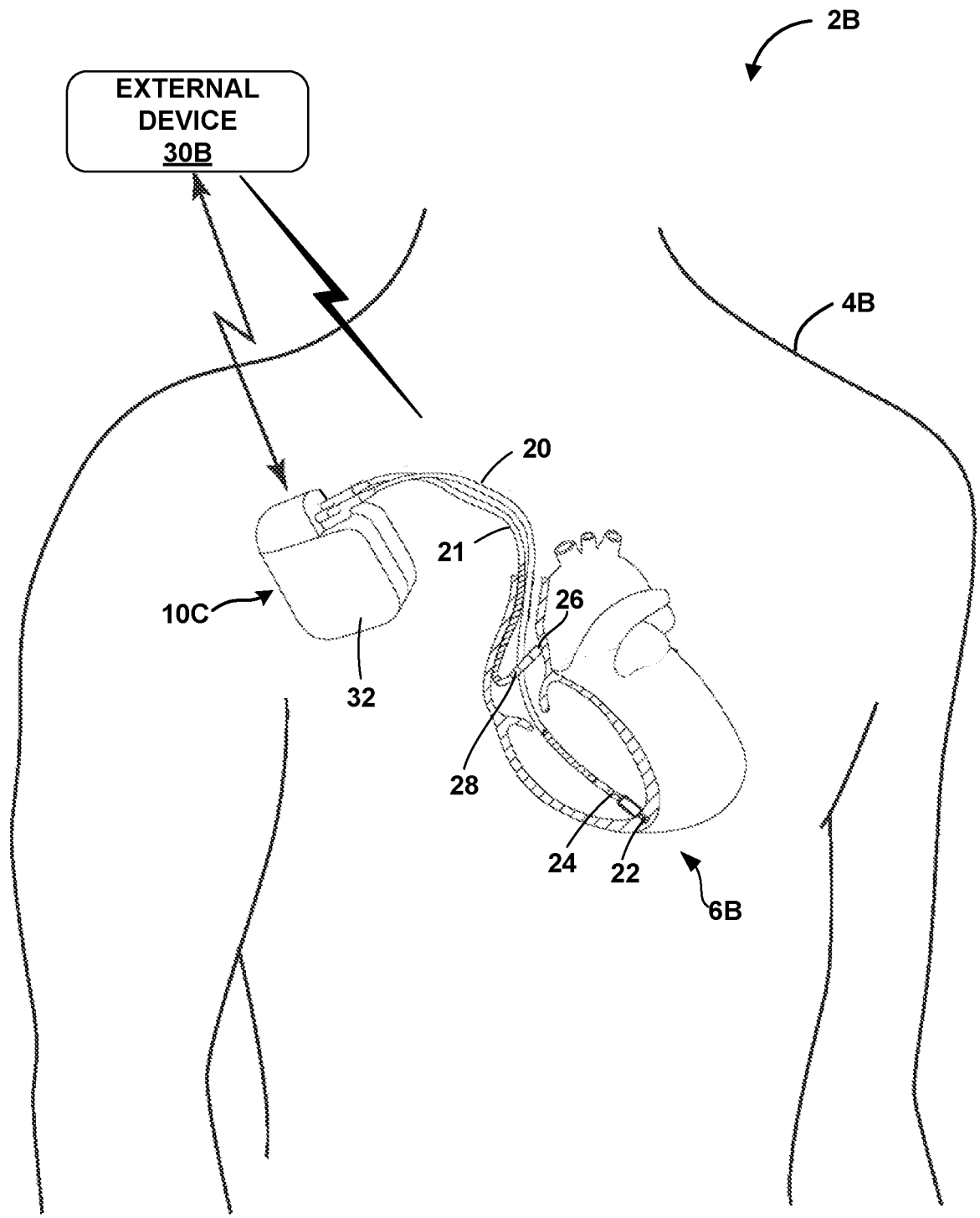
FIG. 3 is a conceptual drawing illustrating another example medical device system in conjunction with a patient, where the medical device system is configured to detect a sleep apnea episode of the patient using cardiac cycle length metrics exhibited by the patient.

FIG. 3 is a conceptual drawing illustrating an example medical device system 2B in conjunction with a patient 4B. Medical device system 2B is an example of a medical device system configured to implement the techniques described herein for detecting an occurrence or likely occurrence of a sleep apnea episode, based on characteristics of cardiac cycle information. In some implementations, upon identifying a likely sleep apnea episode, components of medical system 18 may also responsively provide an alert indicating that a sleep apnea episode is likely occurring, and/or deliver a therapy configured to prevent, mitigate, or remedy the effects of the sleep apnea episode. In the illustrated example, medical device system 2B includes an implantable medical device (IMD) 10C coupled to a ventricular lead 20 and an atrial lead 21.

Ventricular lead 20 and atrial lead 21 are electrically coupled to IMD 10C and extend into the patient's heart 6B. Ventricular lead 20 includes electrodes 22 and 24 shown positioned on the lead in the patient's right ventricle (RV) for sensing ventricular electrogram (EGM) signals and pacing in the RV. Atrial lead 21 includes electrodes 26 and 28 positioned on the lead in the patient's right atrium (RA) for sensing atrial EGM signals and pacing in the RA.

IMD 10C may use both ventricular lead 20 and atrial lead 21 to acquire cardiac electrogram (EGM) signals from heart 6B of patient 4B. Medical device system 2B is shown as having a dual chamber IMD configuration, but other examples may include one or more additional leads, such as a coronary sinus lead extending into the right atrium, through the coronary sinus and into a cardiac vein to position electrodes along the left ventricle (LV) for sensing LV EGM signals and delivering pacing pulses to the LV. In other examples, a medical device system may be a single chamber system, or otherwise not include atrial lead 21.

Processing circuitry, sensing circuitry, and other circuitry configured for performing the techniques described herein are housed within a sealed housing 32. Housing 32 (or a portion thereof) may be conductive so as to serve as an electrode for pacing or sensing. IMD 10C may acquire EGM signal data and cardiac rhythm episode data and transmit the data to an external device 30B. External device 30B may be a computing device, e.g., a device used in a home, ambulatory, clinic, or hospital setting, comprising processing circuitry and/or communicative interfacing circuitry configured to communicate with IMD 10C via wireless telemetry. External device 30B may be coupled to a remote patient monitoring system, such as Carelink®, available from Medtronic plc, of Dublin, Ireland. External device 30B may include, be, or be part of, in various examples, a programmer, external monitor, or consumer device, e.g., a smart phone.

External device 30B may be used to program commands or operating parameters into IMD 10C for controlling its functioning, e.g., when configured as a programmer for IMD 10C. External device 30B may be used to interrogate IMD 10C to retrieve data, including device operational data as well as physiological data accumulated in IMD memory of IMD 10C. The interrogation may be automatic, e.g., according to a schedule, or may be triggered in response to certain stimuli, such as the detection of a remote or local user command. Programmers, external monitors, and consumer devices are examples of external devices 30B that may be used to interrogate IMD 10C. Examples of communication techniques used by IMD 10C and external device 30B include radiofrequency (RF) telemetry, which may be an RF link established via Bluetooth®, WiFi®, or medical implant communication service (MICS).

Medical device system 2B is an example of a medical device system operable to leverage cardiac cycle information to detect likely episodes of sleep apnea. For instance, medical device system 2B may be configured to monitor functional data associated with heart 6B and to use the monitored data to determine whether certain aberrations in the monitored functioning indicate a likely episode of sleep apnea. In some implementations, if medical device system 2B determines that a sleep apnea episode has likely occurred, medical device system 2B may responsively provide an alert indicating that the event is detected, and optionally, trigger delivery of a therapy configured to remediate the effects of the event or stem the progression of such effects. Example therapies that may be delivered to treat sleep apnea include positive airway pressure, e.g., as provided by a continuous positive airway pressure (CPAP) or bilevel positive airway pressure (BiPAP) machine (not shown), or cardiac pacing. The techniques may be performed by processing circuitry of medical device system 2B, such as processing circuitry of one or both of IMD 10C and external device 30B, individually, or collectively.

The processing circuitry of external device 30B and/or IMD 10C may determine the values of at least some patient parameters based on physiological signals generated by sensing circuitry of one or both of IMD 10C, such as a cardiac cycle measurements generated by sensing circuitry of IMD 10C. In some examples, IMD 10C may include or be coupled to one or more other sensors that generate one or more other physiological signals, such as signals that vary based on patient motion and/or posture, blood flow, respiration, or edema. The processing circuitry of external device 30B and/or IMD 10C may determine patient parameters based on therapy delivered by various components of medical device system 2B that are omitted from FIG. 3 for ease of illustration, such as a CPAP machine. For instance, the processing circuitry of external device 30B and/or IMD 10C may analyze cardiac cycle information to determine whether a sleep apnea episode has been remediated effectively by way of therapy delivered by the positive airway pressure machine or IMD 10C.

As described above, the sensing circuitry of IMD 10C or coupled to IMD 10C may gather cardiac cycle information that indicates the physiological function of heart 6B. For instance, IMD 10C may gather R-R interval (RRI) data exhibited by the cardiac function of heart 6B, and provide the RRI data to the processing circuitry of medical device system 18. Using the RRI data, the processing circuitry of medical device system 18 may analyze various types of trends in the heart rate of patient 4B. For instance, the processing circuitry of medical device system 2B may pair the RRIs, using a predetermined number of RRIs between the RRIs. In some implementations, the processing circuitry may pair consecutive RRIs, such as by pairing the first and second recorded RRIs, pairing the third and fourth recorded RRIs, pairing the fifth and sixth recorded RRIs, and so on. For instance, the sensing circuitry of IMD 10C may read the RRI data at intervals of one unit of time, such as one minute (1 min). If the processing circuitry of medical device system 2B is configured to pair consecutive RRIs, then the processing circuitry may pair the RRIs as {RR(i), RR(i−1)}, where 'i' denotes a sequential number of the respective RRI is gathered by the sensing circuitry of IMD 10C.

In other examples, the processing circuitry of medical device system 2B may pair RRIs that are separated by one or more intervening RRIs. For instance, the processing circuitry of medical device system 2B may pair RRIs that occurred 10 intervals apart in a series of intervals, or multiple such choices at the same time. In this example, the RRI pairs formed by the processing circuitry of medical device system 2B may be expressed generically as {RR(i), RR(I−10)}. It will be appreciated that the implementations described above with respect to pairing RRI information at particular intervals is provided purely as an example for discussion, and that other intervals between RRIs may be used in accordance with various configurations consistent with aspects of this disclosure.

In accordance with this disclosure, the processing circuitry of medical device system 2B analyzes trends in the RRI information to detect a sleep apnea episode or a likely sleep apnea episode. In some examples, the processing circuitry of medical device system 2B directly analyzes the trends in the RRI information as a function of time. In other examples, the processing circuitry of medical device system 2B analyzes the RRI pairings that are formed as described above. For instance, the processing circuitry of medical device system 2B may analyze the structure of a Lorenz plot of the respective RRI deltas (denoted by "dRR") exhibited by the RRI pairs that are formed as described above.

Figure 4:
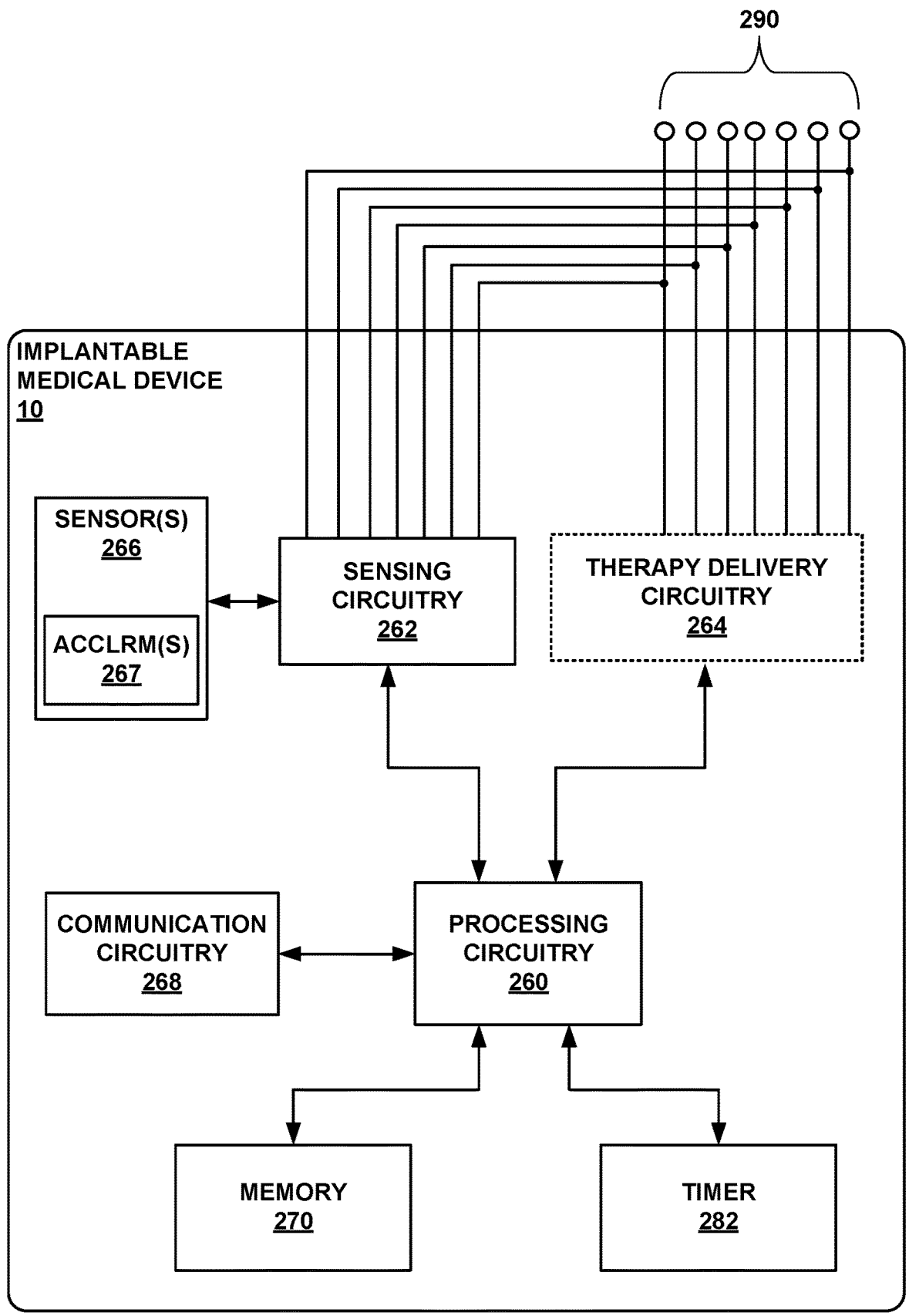
FIG. 4 is a functional block diagram illustrating an example configuration of an implantable medical device (IMD) configured to sense and record cardiac electrogram signals of a patient.

FIG. 4 is a functional block diagram illustrating an example configuration of IMD 10. IMD 10 may correspond to ICM 10A in FIG. 1, ICM 10B in FIG. 2, IMD 10C illustrated in FIG. 3, or another IMD configured to implement the techniques for determining whether to store or discard cardiovascular pressure measurements as described in this disclosure. In the illustrated example, IMD 10 includes processing circuitry 260 and an associated memory 270, sensing circuitry 262, therapy delivery circuitry 264, one or more sensors 266, and communication circuitry 268. However, IMD 10 need not include all of these components in some implementations, or may include additional components in some implementations. For example, IMD 10 may not include therapy delivery circuitry 264 in some instances, such as when implemented as ICM 10A or 10B.

Memory 270 includes computer-readable instructions that, when executed by processing circuitry 260, cause IMD 10 and processing circuitry 260 to perform various functions attributed to IMD 10 and processing circuitry 260 herein (e.g., determining time of day, comparing time of day to a predetermined window, determining posture, comparing posture to target posture, and causing communication circuitry 268 to transmit cardiovascular pressure measurements to an external device). Memory 270 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media. Memory 270 may store threshold(s) for time of day, posture, heart rate, activity level, respiration rate, and other parameters. Memory 270 may also store data indicating cardiovascular pressure measurements received from a pressure sensing device 11.

Processing circuitry 260 may include fixed function circuitry and/or programmable processing circuitry. Processing circuitry 260 may include any one or more of a microprocessor, a controller, a digital signal processor (DSP), an application specific integrated circuit (ASIC), a field-programmable gate array (FPGA), or equivalent discrete or analog logic circuitry. In some examples, processing circuitry 260 may include multiple components, such as any combination of one or more microprocessors, one or more controllers, one or more DSPs, one or more ASICs, or one or more FPGAs, as well as other discrete or integrated logic circuitry. The functions attributed to processing circuitry 260 herein may be embodied as software, firmware, hardware or any combination thereof.

Sensing circuitry 262 and therapy delivery circuitry 264 are coupled to electrodes 290. Electrodes 290 illustrated in FIG. 4 may correspond to, for example, electrodes carried on leads 21 and/or 22 of medical device system 2B (FIG. 3), or electrodes 22 and 24 of ICM 10B. Sensing circuitry 262 may monitor signals from a selected two or more of electrodes 290 in order to monitor electrical activity of heart, impedance, or other electrical phenomenon. Sensing of a cardiac electrical signal may be done to determine heart rates or heart rate variability, or to detect arrhythmias (e.g., tachyarrhythmias or bradycardia) or other electrical signals. In some examples, sensing circuitry 262 may include one or more filters and amplifiers for filtering and amplifying a signal received from electrodes 290. In some examples, sensing circuitry 262 may sense or detect physiological parameters, such as heart rate, blood pressure, respiration, and the like.

The resulting cardiac electrical signal may be passed to cardiac event detection circuitry that detects a cardiac event when the cardiac electrical signal crosses a sensing threshold. The cardiac event detection circuitry may include a rectifier, filter and/or amplifier, a sense amplifier, comparator, and/or analog-to-digital converter. Sensing circuitry 262 outputs an indication to processing circuitry 260 in response to sensing of a cardiac event (e.g., detected P-waves or R-waves).

In this manner, processing circuitry 260 may receive detected cardiac event signals corresponding to the occurrence of detected R-waves and P-waves in the respective chambers of heart. Indications of detected R-waves and P-waves may be used for detecting ventricular and/or atrial tachyarrhythmia episodes, e.g., ventricular or atrial fibrillation episodes. Some detection channels may be configured to detect cardiac events, such as P- or R-waves, and provide indications of the occurrences of such events to processing circuitry 260, e.g., as described in U.S. Pat. No. 5,117,824 to Keimel et al., which issued on Jun. 2, 1992 and is entitled, "APPARATUS FOR MONITORING ELECTRICAL PHYSIOLOGIC SIGNALS," and is incorporated herein by reference in its entirety.

Sensing circuitry 262 may also include a switch module to select which of the available electrodes 290 (or electrode polarities) are used to sense the heart activity. In examples with several electrodes 290, processing circuitry 260 may select the electrodes that function as sense electrodes, i.e., select the sensing configuration, via the switch module within sensing circuitry 262. Sensing circuitry 262 may also pass one or more digitized EGM signals to processing circuitry 260 for analysis, e.g., for use in cardiac rhythm discrimination.

In the example of FIG. 4, IMD 10 includes one or more sensors 266 coupled to sensing circuitry 262. Although illustrated in FIG. 4 as included within IMD 10, one or more of sensors 266 may be external to IMD 10, e.g., coupled to IMD 10 via one or more leads, or configured to wirelessly communicate with IMD 10. In some examples, sensors 266 transduce a signal indicative of a patient parameter, which may be amplified, filtered, or otherwise processed by sensing circuitry 262. In such examples, processing circuitry 260 determines values of patient parameters based on the signals. In some examples, sensors 266 determine the patient parameter values, and communicate them, e.g., via a wired or wireless connection, to processing circuitry 260.

In some examples, sensors 266 include one or more accelerometers 267, e.g., one or more three-axis accelerometers. Signals generated by the one or more accelerometers 267 may be indicative of, as examples, gross body movement (e.g., activity) of the patient, patient posture, heart sounds or other vibrations or movement associated with the beating of the heart, or coughing, rales, or other respiration abnormalities. Accelerometers 267 may produce and transmit signals to processing circuit 260 for a determination as to whether the heart 4 has contracted. In some examples, sensors 266 include one or more microphones configured to detect heart sounds or respiration abnormalities, and/or other sensors configured to detect patient activity or posture, such as gyroscopes and/or strain gauges. In some examples, sensors 266 may include sensors configured to transduce signals indicative of blood flow, oxygen saturation of blood, or patient temperature, and processing circuitry 260 may determine patient parameters values based on these signals.

Therapy delivery circuitry 264 is configured to generate and deliver electrical therapy to the heart. Therapy delivery circuitry 264 may include one or more pulse generators, capacitors, and/or other components capable of generating and/or storing energy to deliver as pacing therapy, defibrillation therapy, cardioversion therapy, other therapy or a combination of therapies. In some instances, therapy delivery circuitry 264 may include a first set of components configured to provide pacing therapy and a second set of components configured to provide anti-tachyarrhythmia shock therapy. In other instances, therapy delivery circuitry 264 may utilize the same set of components to provide both pacing and anti-tachyarrhythmia shock therapy. In still other instances, therapy delivery circuitry 264 may share some of the pacing and shock therapy components while using other components solely for pacing or shock delivery.

Therapy delivery circuitry 264 may include charging circuitry, one or more charge storage devices, such as one or more capacitors, and switching circuitry that controls when the capacitor(s) are discharged to electrodes 290 and the widths of pulses. Charging of capacitors to a programmed pulse amplitude and discharging of the capacitors for a programmed pulse width may be performed by therapy delivery circuitry 264 according to control signals received from processing circuitry 260, which are provided by processing circuitry 260 according to parameters stored in memory 270. Processing circuitry 260 controls therapy delivery circuitry 264 to deliver the generated therapy to the heart via one or more combinations of electrodes 290, e.g., according to parameters stored in memory 270. Therapy delivery circuitry 264 may include switch circuitry to select which of the available electrodes 290 are used to deliver the therapy, e.g., as controlled by processing circuitry 260.

Communication circuitry 268 includes any suitable hardware, firmware, software or any combination thereof for communicating with another device, such as an external device 30 or another IMD or sensor. Under the control of processing circuitry 260, communication circuitry 268 may receive downlink telemetry from and send uplink telemetry to an external device 30 or another device with the aid of an antenna, which may be internal and/or external. In some examples, communication circuitry 268 may communicate with a local external device, and processing circuitry 260 may communicate with a networked computing device via the local external device and a computer network, such as the Medtronic CareLink® Network developed by Medtronic, plc, of Dublin, Ireland.

A clinician or other user may retrieve data from IMD 10 using external device 30A or another local or networked computing device configured to communicate with processing circuitry 260 via communication circuitry 268. The clinician may also program parameters of IMD 10 using external device 30 or another local or networked computing device.

Communication circuitry 268 may also be configured to communicate with an implantable pressure sensing device 11. Processing circuitry 260 may receive measured cardiovascular pressure values, e.g., PAP values, from pressure sensing device 11 via communication circuitry 268. In some examples, processing circuitry 260 may send a trigger signal to sensing device 11 via communication circuitry 268 to control the sensing device to measure cardiovascular pressure in response to the trigger signal.

Although not illustrated in FIG. 4, communication circuitry 268 may be coupled or coupleable to electrodes 290 for tissue conductance communication (TCC) via the electrodes. In some examples, communication with IMD 10 and external device 30 may be via RF telemetry or TCC. In one example, communication circuitry 268 may be configured for RF telemetry communication with external device 30 and TCC with pressure sensing device 11.

Figure 5:
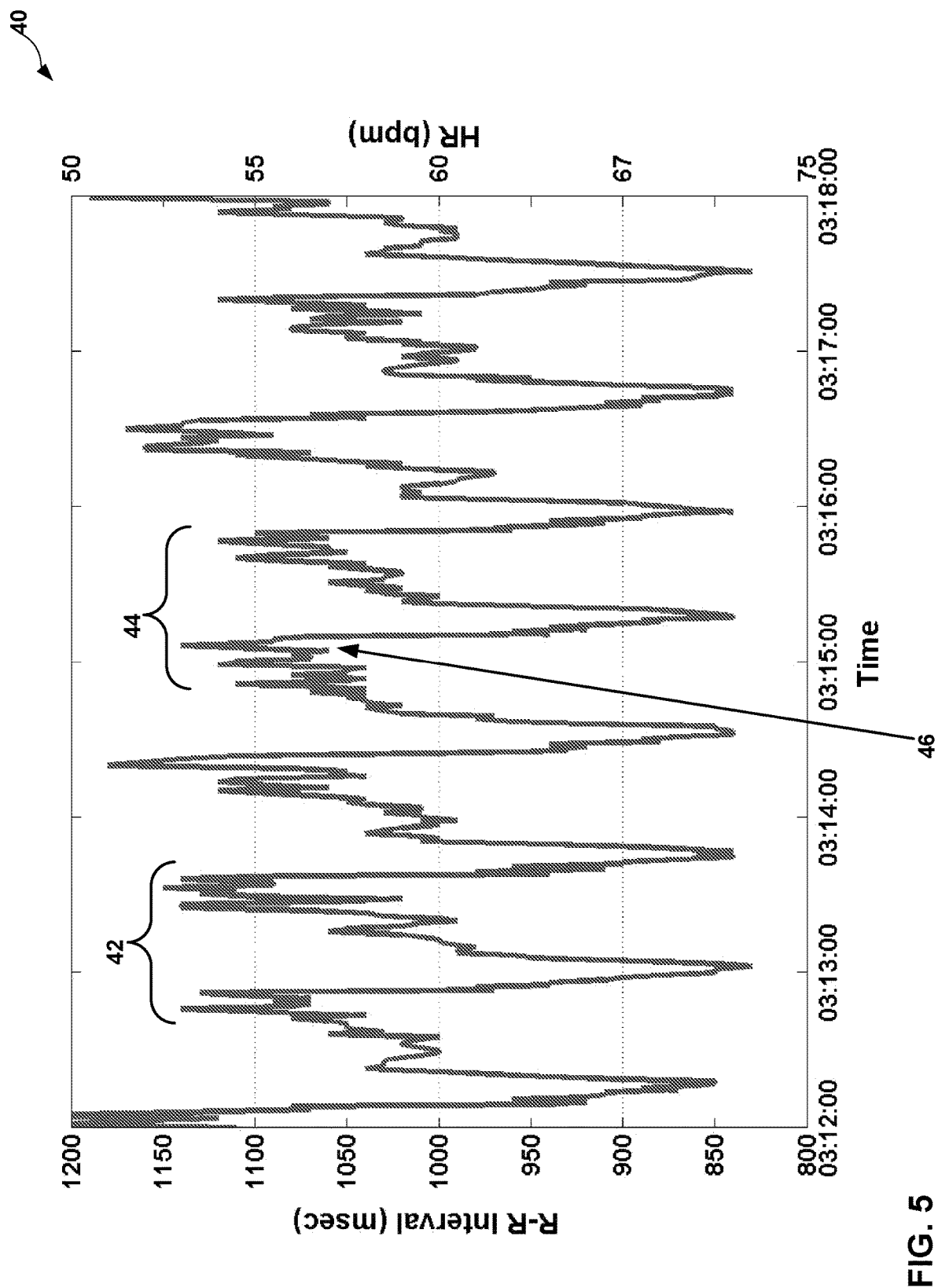
FIG. 5 is a line graph that illustrates sleep disordered heart rate (SDHR) information for a patient.

FIG. 5 is a line graph 40 that illustrates sleep disordered heart rate (SDHR) information for patient 4. In the example of line graph 40, the SDHR of patient 4 exhibits, at various times, characteristics of different physiological conditions. For instance, the processing circuitry of medical device system 2A or 2B (collectively "medical device system 2"), such as processing circuitry of an IMD 10 and/or external device 30, may analyze trends shown by clusters of maxima and minima (e.g., "crest" and "trough") points of line graph 40 to determine whether patient 4 exhibits symptoms of a chronic condition or a single episode of such a chronic condition. Some crest-and-trough clusters that the processing circuitry of medical device system 2 may analyze to detect possible sleep apnea episodes with respect to a patient 4 are called out in FIG. 5.

For example, even during normal breathing, the heart rate information of line graph 40 illustrates a type of cyclical variable heart rate (CVHR) referred to as respiratory sinus arrhythmia (RSA). During RSA, the heart rate of patient 4 increases with an inspiration (or inhalation) and the heart rate of patient 4 decreases with expiration (or exhalation). RSA is associated with a single breath cycle, e.g., a single heart rate increase with inspiration and a single heart rate decrease with expiration. RSA is illustrated in the graph of FIG. 5 by the higher frequency and lower amplitude variations, e.g., with areas 42 and 44.

The lower frequency and higher amplitude variations of the graph of FIG. 5, on the other hand, illustrate a form of CVHR, referred to herein as SDHR, associated with sleep apnea. For example, each of areas 42 and 44 illustrate one apnea arousal cycle, and the corresponding decrease and increase in heart rate or cardiac cycle length. In most patients, a decrease of heart rate is observed during each apnea event followed by an increase of heart rate near the end of the apnea event. The heart rate further increases during ensuing hyperventilation. In the example of the individual sleep apnea episode associated with area 44 of line graph 40, the heart rate increase due to autonomic arousal is indicated by crest 46. For instance, crest 46 may indicate a heart rate increase that heart 6 experiences as the autonomic nervous system of patient 4 attempts to compensate for the decreased oxygen saturation during the pulmonary malfunction of a sleep apnea episode. As such, crest 46 may be indicative of a period of overexertion of heart 6 which results from compensatory mechanisms that the autonomic nervous system of patient 4 implements to counter the decreased oxygen saturation caused by the sleep apnea episode.

Again, the processing circuitry of medical device system 2 or 18 may collect and analyze R-R intervals, or cardiac cycle lengths determined in any way, to identify apnea events based the variability characteristics illustrated by the line graph 40 of FIG. 5. For example, line graph 40, or a data flow that is expressed as line graph 40 to be understandable to a human reader, using RRI information that sensing circuitry 262 of IMD 10 gathers by monitoring the activity of heart 6. In turn, the processing circuitry of medical device system 2 or 18 may analyze the data corresponding to area 44 to detect a sleep apnea episode likely experienced by patient 4.

Figure 6:
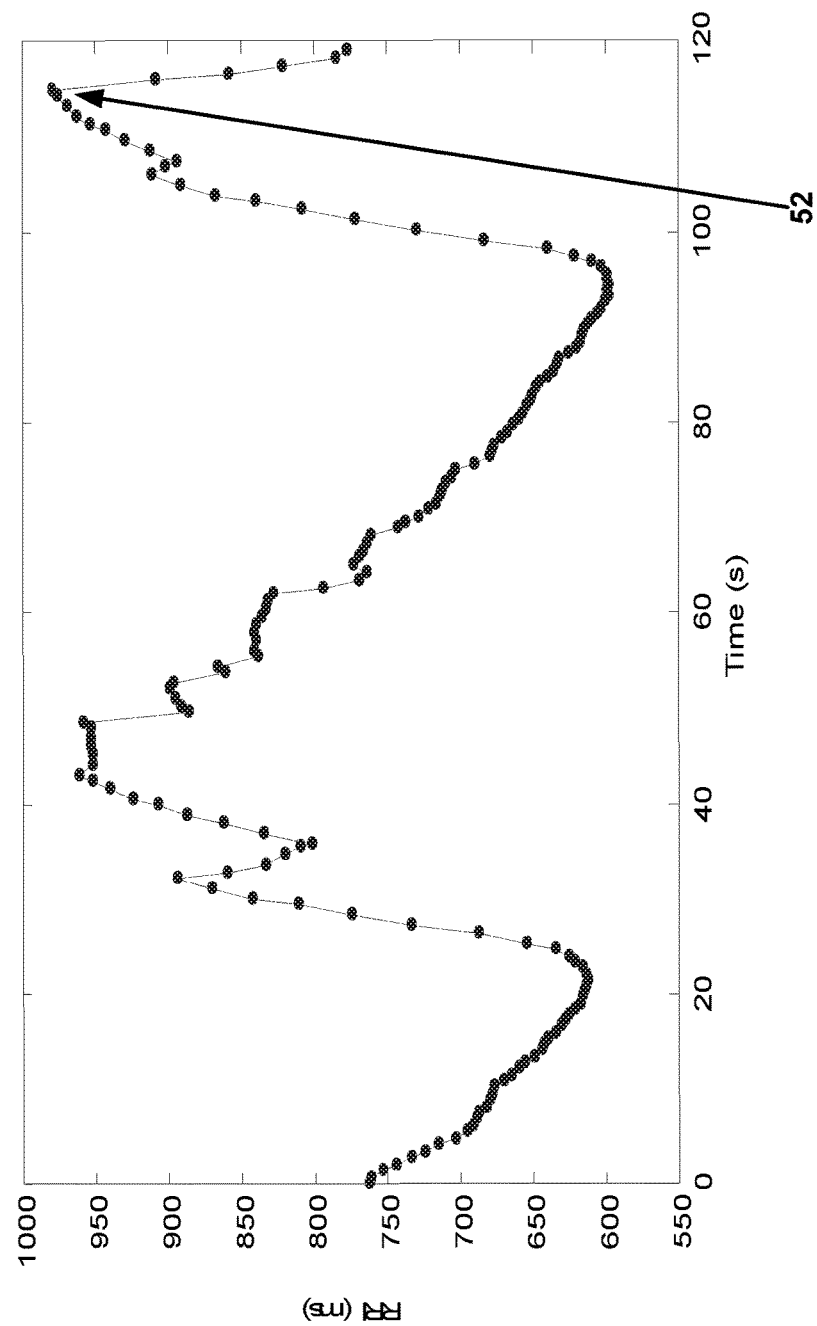
FIG. 6 is a line graph that illustrates measurements associated with a sleep apnea arousal cycle for a patient.

FIG. 6 is a line graph 50 that illustrates measurements associated with a sleep apnea arousal cycle that spans approximately 120 seconds of time. The RRI information illustrated in line graph 50 may represent a portion of area 46 illustrated in line graph 40 of FIG. 5. During the 120-second time period represented by line graph 50, the heart rate of heart 6B may exhibit a variability pattern that is associated with an individual episode of sleep apnea. Moreover, the final crest (the rightmost maxima) 52 of line graph 50 is higher than the remaining crests. Final crest 52 illustrates a possible overexertion of heart 6 toward the end of the sleep apnea episode. Again the possible overexertion represented by final crest 52 may be caused by an autonomic compensatory reaction of heart 6 in response to the drop in oxygen saturation due to the breathing irregularity of the sleep apnea episode.

Figure 7:
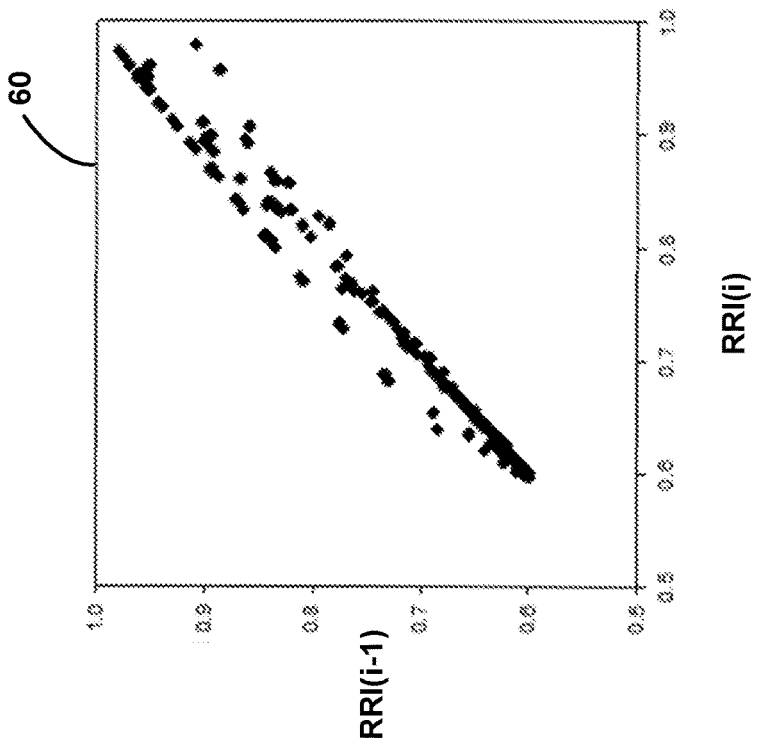
FIG. 7 is a Lorenz plot that plots the values of consecutive measured R-R intervals against each other.

FIG. 7 is a Lorenz plot 60 that plots the values of consecutive measured R-R intervals against each other. As discussed above, R-R intervals (or RRIs) may be used as one method to determine the cardiac cycle length of consecutive heart beats of heart 6 within patient 4. The processing circuitry of medical device system 2 may use changes in R-R intervals may to determine a degree of variability of the cardiac cycle lengths. R-R interval changes, and the characteristics of the distribution shown in Lorenz plot 60 may be indicative of various pulmonary conditions, including states of normal breathing, or episodes of RSA or sleep apnea. For instance, the processing circuitry of medical device system 2 may use the dispersedness, or level of dispersion, of plot points on a Lorenz plot of RRI value pairs to detect various conditions of patient 4. According to the aspects of this disclosure, the processing circuitry of medical device system 2 may detect pulmonary conditions, such as an ongoing episode of sleep apnea, using the level of dispersion of the RRI Lorenz plot.

In various situations, RRI changes may have a low, medium, or high degree of variability as the changes are scattered throughout the Lorenz plot. As shown in FIG. 7, Lorenz plot 60 maps a current RRI value against a corresponding RRI value that was measured just prior to the current RRI. The current RRI, serialized with a value 'i' is plotted on the horizontal (x-) axis of Lorenz plot 60. The prior RRI value, serialized with a value 'i−1' is plotted on the vertical (y-) axis of Lorenz plot 60.

In general, the processing circuitry of medical device system 2 may determine that a "tighter" dispersion of an RRI(i) vs. RRI(i−1) Lorenz plot is associated with normal functioning of the pulmonary system. Additionally, the processing circuitry of medical device system 2 may detect different conditions based on the degree of dispersion of an RRI(i) vs. RRI(i−1) Lorenz plot. In various examples, the processing circuitry of medical device system 2 may implement pattern recognition (including, but not limited to pattern matching) technology to map the degree of dispersion of an RRI(i) vs. RRI(i−1) Lorenz plot to a particular condition. With respect to the particular example of Lorenz plot 60 illustrated in FIG. 7, the processing circuitry of medical device system 2 may determine that the degree of dispersion or directional scatter of the RRI(i) vs. RRI(i−1) plot points are associated with an individual episode or ongoing condition of respiratory sinus arrhythmia. For instance, the processing circuitry of medical device system 2 may determine that the degree of dispersion of Lorenz plot 60 is within a threshold deviation from a predetermined degree of dispersion.

Figure 8:
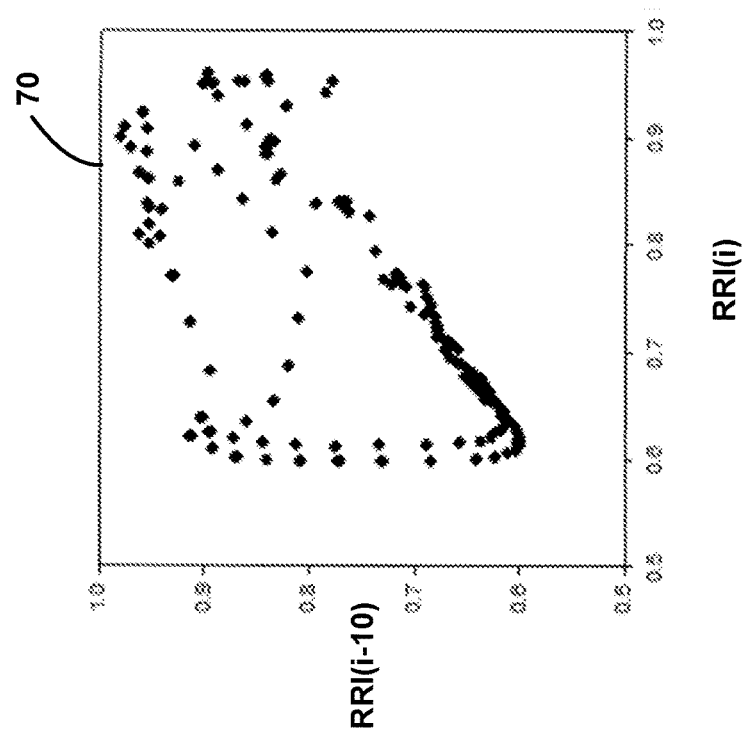
FIG. 8 is a Lorenz plot illustrating a distribution of cardiac cycle length metric values that a medical device system configured according to aspects of this disclosure may use to detect a sleep apnea episode of a patient.

FIG. 8 is a Lorenz plot 70 illustrating a distribution of cardiac cycle length metric values that medical device system 2 may use to detect a sleep apnea episode of patient 4. Sensing circuitry 262 of or coupled to IMD 10 may sense a cardiac signal from heart 6. For instance, the cardiac signal may vary as a function of a cardiac cycle of patient 4. IMD 10 may form data from the sensed cardiac signal metric values and variations thereof, such as data that can be stored and/or communicated with other devices. In turn, communication circuitry 268 of IMD 10 or coupled to IMD 10 may communicate the cardiac cycle metric value data to external device 30, or may communicate alert information to external device 30.

Processing circuitry of IMD 10 and/or external device 30 may use the cardiac signal-related data received via the communication circuitry to determine a series of consecutive cardiac cycle length metric values based on the cardiac signal sensed by the sensing circuitry of IMD 10. Each cardiac cycle length measurement may correspond to an RRI described above. The processing circuitry of IMD 10 and/or external device 30 may pair the cardiac cycle lengths based on how many intervening cardiac cycle length metrics were measured between the respective cardiac cycle length metrics of each pair. An integer value of 'n' denotes the number of intervening cardiac cycle length metrics that are measured between the respective metrics of each pair formed by the processing circuitry of IMD 10 and/or external device 30. As used herein, the term "cardiac cycle length metrics" may include cardiac cycle lengths and/or delta information between multiple cardiac cycle lengths.

For instance, in an implementation in which each pair includes directly consecutive cardiac cycle length metrics (i.e., no other cardiac cycle length metrics are detected between the respective metrics of each pair), n may have a value of one (1). An example in which the processing circuitry of IMD 10 and/or external device 30 identifies pairs of cardiac cycle length metrics using a zero value for n is illustrated in Lorenz plot 60 of FIG. 7. As described above, Lorenz plot 60 plots consecutive RRIs (i.e., with no intervening RRIs measured between them) against each other.

Lorenz plot 70 of FIG. 8 illustrates an example in which the processing circuitry of a medical device system 2, e.g., processing circuitry of an IMD 10 and/or external device 30, identifies multiple pairs of cardiac cycle length metrics, such that the each of the identified pairs is separated by ten (10) of the cardiac cycle length metrics. In other words, in the particular example of constructing the distribution illustrated in Lorenz plot 70, the processing circuitry of IMD 10 and/or external device 30 may set the value of n as ten. Additionally, the processing circuitry of IMD 10 and/or external device 30 may construct the distribution illustrated in Lorenz plot 70 by mapping the two respective cardiac cycle length metrics of each identified pair against each other on the horizontal (x-) and vertical (y-) axes of Lorenz plot 70.

The processing circuitry of IMD 10 and/or external device 30 may analyze one or more characteristics of the constructed distribution illustrated by Lorenz plot 70 to determine various conditions being exhibited by patient 4, such as by detecting an individual episode of a chronic condition. In other examples, the processing circuitry of IMD 10 and/or external device 30 may arrange pairs of cardiac cycle length metrics in bins, based on the occurrence time (e.g., as illustrated in Lorenz plot 70), and analyze the bins to determine dispersedness or directional scatter (e.g., the degree of dispersion). For instance, the processing circuitry of IMD 10 and/or external device 30 may determine distances between neighboring metrics, or between each metric and a static origin line. For instance, the processing circuitry of IMD 10 and/or external device 30 may determine that a bin with a greater number of pairs shows a greater degree of clustering, while a bin with a lesser number of pairs or no pairs shows a lower (or potentially zero) degree of clustering. Moreover, by implementing various aspects of this disclosure, the processing circuitry of IMD 10 and/or external device 30 may analyze the characteristics of Lorenz plot 70 to detect cardiovascular conditions and/or conditions stemming from other bodily systems, by using the cardiac cycle length metrics that are used to construct the distribution shown in Lorenz plot 70.

In the particular example of Lorenz plot 70, various characteristics of the distribution of cardiac cycle length metrics constructed by the processing circuitry of IMD 10 and/or external device 30 (hereinafter, generically, "processing circuitry of medical device system 2") indicate a likely episode of sleep apnea. More specifically, the RRI(i) vs. RRI(i−10) distribution constructed by external device 30C and expressed by way of Lorenz plot 70 is a cardiac cycle length pattern that shows heart 6's response to the decrease in oxygen saturation caused by the pulmonary dysfunction of a currently-occurring episode of sleep apnea. In the example of Lorenz plot 70, the processing circuitry of medical device system 2 may use cardiac cycle lengths (e.g., the plotted RRIs) as the cardiac cycle length metrics to be analyzed for detecting an episode of sleep apnea. An example of distribution characteristics of Lorenz plot 70 that the processing circuitry of medical device system 2 may use to detect the sleep apnea episode is dispersion-related. For instance, the processing circuitry of medical device system 2 may determine dispersion or directional scatter information with respect to a subset or a totality of the plot points included in the constructed distribution that is illustrated in Lorenz plot 70. In the particular example of Lorenz plot 70, the processing circuitry of medical device system 2 may detect the sleep apnea condition based on the dispersion (directional scatter) information determined with respect to the constructed distribution of cardiac cycle lengths as plotted.

According to some examples, the processing circuitry of medical device system 2 may quantify the dispersion (directional scatter) information of Lorenz plot 70. In turn, the processing circuitry of medical device system 2 may compare the dispersion (directional scatter) information of the constructed distribution shown in (e.g., as quantified) to a threshold level of dispersion. If the processing circuitry determines that the level of dispersion is above the predetermined threshold level.

In some examples, the processing circuitry of medical device system 2 may use a so-called "unity line" to determine whether the dispersion (directional scatter) information for the constructed distribution of cardiac cycle lengths shown in Lorenz plot 70. For instance, the processing circuitry of medical device system 2 may construct a unity line that connects hypothetical RRI(i) vs. RRI(i−10) plot points that are associated with a disorder-free progression of cardiac lengths. The processing circuitry of medical device system 2 may determine a difference between the degree of dispersion of the constructed distribution of Lorenz plot 70 to the degree of dispersion of the unity line to obtain the dispersion (directional scatter) information with which to detect the sleep apnea episode.

In some examples, the processing circuitry of medical device system 2 may determine one or more clustering characteristics of Lorenz plot 70. For instance, the processing circuitry of medical device system 2 may determine information indicating various groupings, or clusters of plot points over the constructed distribution of Lorenz plot 70. In turn, the processing circuitry of medical device system 2 may use the clustering characteristic(s) of the constructed distribution of Lorenz plot 70 to detect the sleep apnea episode of patient 4. For instance, the processing circuitry of medical device system 2 may compare the clustering characteristic(s) of the constructed distribution of Lorenz plot 70 to a threshold. In this example, if the compared clustering characteristic(s) of Lorenz plot 70 exceed the clustering threshold, then the processing circuitry of medical device system 2 may detect the sleep apnea episode of patient 4 based on the determined clustering characteristic(s).

According to various implementations, the processing circuitry of medical device system 2 may detect a sleep apnea episode based on a particular variability magnitudes detected from the distribution expressed by way of Lorenz plot 70. For instance, the processing circuitry of medical device system 2 may detect a sleep apnea episode if the processing circuitry of medical device system 2 determines that the plotted points are positioned within a particular proximity of a unity line. In some examples, the processing circuitry of medical device system 2 may detect a sleep apnea episode if the plot points are positioned within the predetermined proximity and if both the RR(i) and RR(i−n) dimensions have greater than a predetermined time duration, denoted by 'X.' In one example, the processing circuitry of medical device system 2 may set the value of X (the predetermined time duration) at three hundred milliseconds (300 ms).

In some examples, the processing circuitry of medical device system 2 may implement trend-spotting, such as a "counting up scheme" to determine whether the distribution illustrated in Lorenz plot 70 indicates a sleep apnea episode. For instance, if the processing circuitry of medical device system 2 detects a predetermined ratio of increasing or decreasing values within a range of consecutive plot points, then the processing circuitry of medical device system 2 may detect a sleep apnea episode. In one example, the processing circuitry of medical device system 2 may detect a sleep apnea episode if the processing circuitry of medical device system 2 detects that at least five (5) out of seven (7) consecutive plot points exhibit an increase over or decrease below the previous plot point. Stated generically, the processing circuitry of medical device system 2 may detect a sleep apnea episode if the processing circuitry of medical device system 2 determines that 'X' out of 'Y' plot points show an increase or decrease. In these and other examples, the processing circuitry of medical device system 2 may implement the trend-spotting scheme using plot points that show an increase or decrease from the respective previous plot point. For instance, the processing circuitry of medical device system 2 may detect the sleep apnea episode if 'X' out of 'Y' consecutive plot points exhibit a decrease in comparison to their respective preceding plot points.

Figure 9:
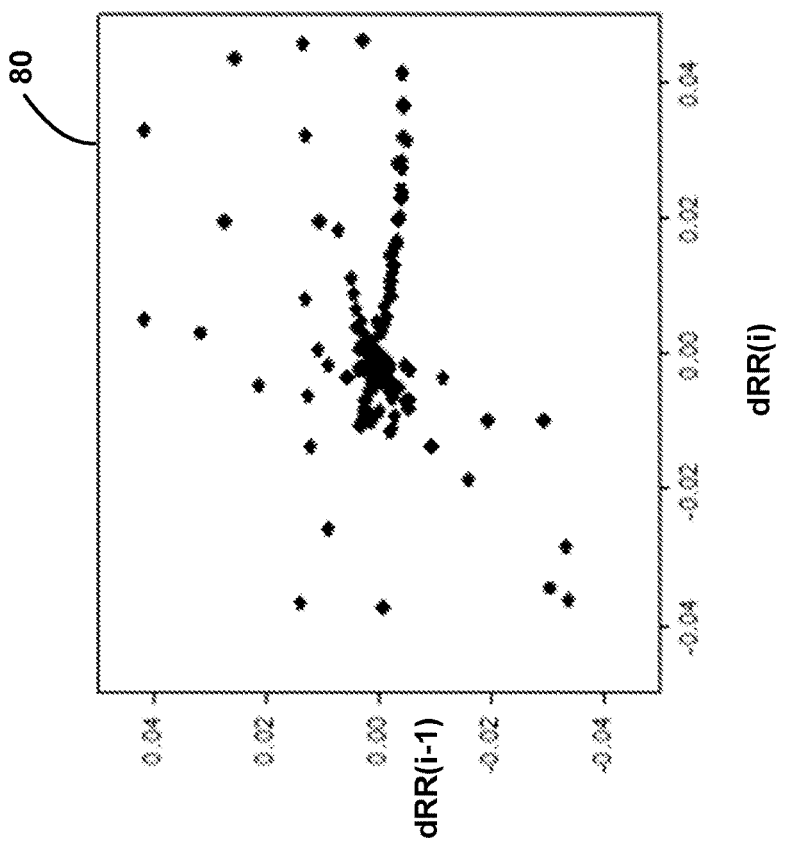
FIG. 9 is a Lorenz plot that plots cardiac cycle length metric values that each expresses a difference between values of two consecutive cardiac cycle lengths from a series of consecutive cardiac cycle lengths.

FIG. 9 illustrates Lorenz plot 80 that plots cardiac cycle length metric values that each expresses a difference between values of two consecutive cardiac cycle lengths from a series of consecutive cardiac cycle lengths. For instance, each value along each of the horizontal (x-) and vertical (y-) axes represents a delta RRI or 'dRRI' in Lorenz plot 80. As such, Lorenz plot 80 represents a dRR(i) vs. dRR(i−1) plot.

The dRRI data represented in Lorenz plot 80 may generally correspond to the RRI data represented in Lorenz plot 60 of FIG. 7. That is, each value represented on an axis of Lorenz plot 80 may represent a first derivative of the corresponding value represented on the corresponding axis of Lorenz plot 60. Moreover, in examples where the processing circuitry of IMD 10 and/or external device 30 uses dRRI data to detect conditions with respect to patient 4, the processing circuitry of medical device system 2 may use the dRRI plotted on Lorenz plot 80 to detect an episode of RSA with respect to patient 4. For instance, the processing circuitry of medical device system 2 may analyze dispersion (directional scatter) information of the constructed distribution of differences between values of two consecutive cardiac cycle lengths of the series of measured cardiac cycle lengths as shown in Lorenz plot 80. Based on the analyzed dispersion (directional scatter) information, such as a determined degree of dispersion and/or clustering information of the distribution, the processing circuitry of IMD 10 and/or external device 30 may detect an episode of RSA during the time window over which the plotted dRRI data was sensed by the sensing circuitry of IMD 10.

Figure 10:
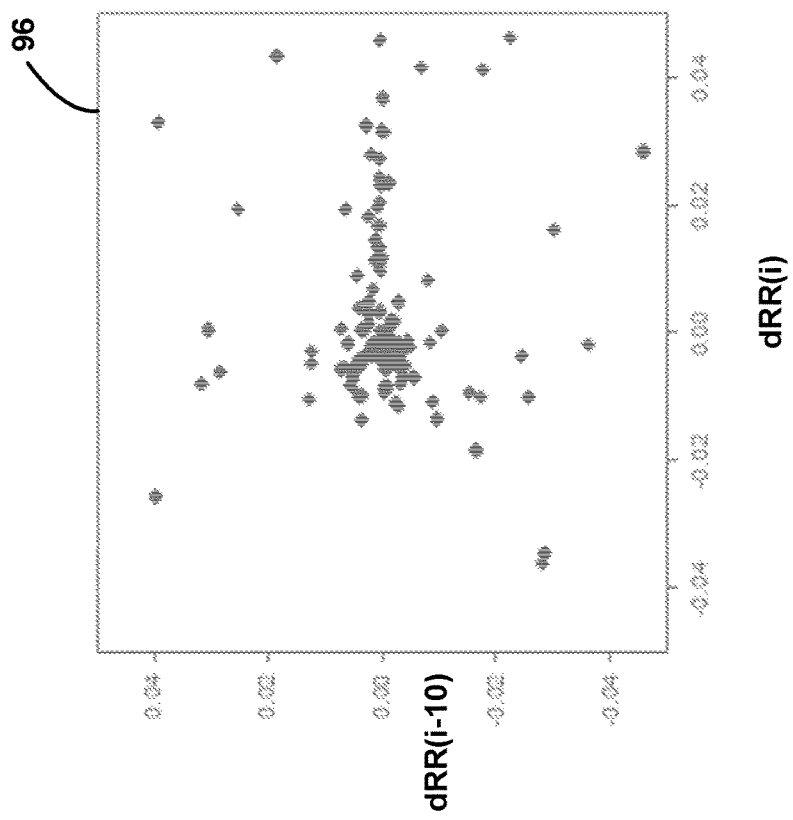
FIG. 10 is a Lorenz plot that plots cardiac cycle length metric values that each expresses a difference between values of two consecutive cardiac cycle lengths from a series of consecutive cardiac cycle lengths.

FIG. 10 illustrates Lorenz plot 96 that plots cardiac cycle length metric values that each expresses a difference between values of two consecutive cardiac cycle lengths from a series of consecutive cardiac cycle lengths. Each value along each of the horizontal (x-) and vertical (y-) axes represents a delta RRI or 'dRRI' in Lorenz plot 96. As such, Lorenz plot 96 represents a dRR(i) vs. dRR(i–10) plot. The dRRI data represented in Lorenz plot 96 generally corresponds to the RRI data represented in Lorenz plot 70 of FIG. 8. That is, each value represented on an axis of Lorenz plot 96 may represent a first derivative of the corresponding value represented on the corresponding axis of Lorenz plot 70 illustrated in FIG. 8. As used herein, the term "cardiac cycle length metric" represents a genus that may include cardiac cycle lengths and/or the first derivate of cardiac cycle lengths (such as dRRI values).

Moreover, in examples where the processing circuitry of medical device system 2 uses dRRI data to detect conditions with respect to patient 4, the processing circuitry of IMD 10 and/or external device 30 may use the dRRI plotted on Lorenz plot 96 to detect an episode of sleep apnea exhibited via the differences between values of two consecutive cardiac cycle lengths from the series of consecutive cardiac cycle lengths gathered by the sensing circuitry of IMD 10 during a finite time window. According to some implementations of the techniques of this disclosure, the sensing circuitry of IMD 10 may gather cardiac cycle length metrics in two-minute (2 min) windows of time. In turn, the processing circuitry may construct the distribution represented by Lorenz plot 96 using the cardiac cycle length metrics gathered during the respective two-minute window.

For instance, the processing circuitry of medical device system 2 may analyze dispersion (directional scatter) information of the constructed distribution of differences between values of two consecutive cardiac cycle lengths of the series of measured cardiac cycle lengths as shown in Lorenz plot 96. Based on the analyzed dispersion (directional scatter) information, such as a determined degree of dispersion (directional scatter) and/or clustering information of the distribution, the processing circuitry of medical device system 2 may detect an episode of sleep apnea exhibited by patient 4 during the time window over which the plotted dRRI data was sensed by the sensing circuitry of IMD 10. In this way, the processing circuitry of medical device system 2 may detect a sleep apnea episode of patient 4 by leveraging cardiac cycle metrics exhibited by heart 6, instead of raising the need to implement a separate monitoring system for pulmonary measurements of patient 4.

Figure 11:
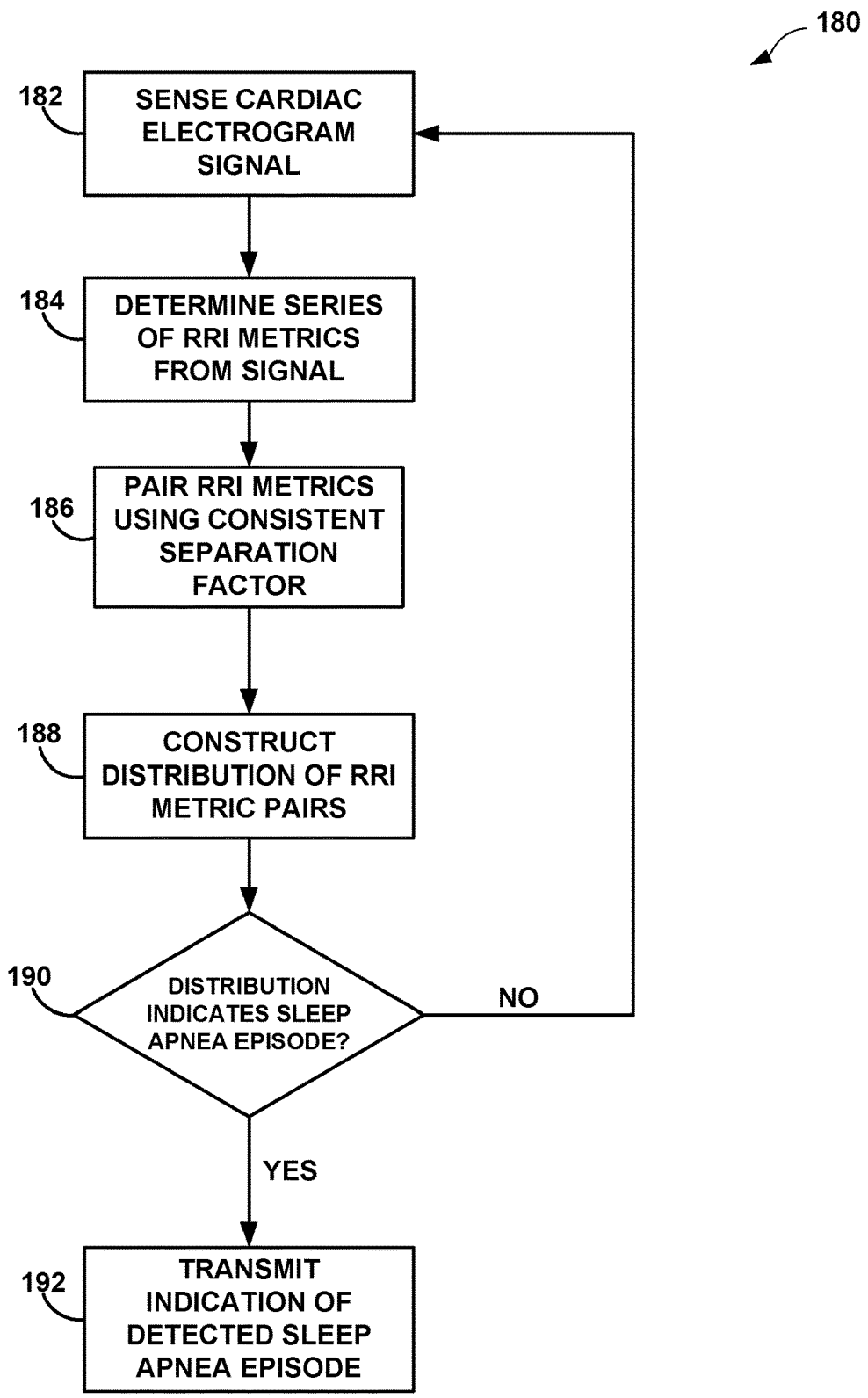
FIG. 11 is a flowchart illustrating an example process by which a medical device system that is configured according to aspects of this disclosure may detect a sleep apnea episode using cardiac cycle length metrics of a patient.

FIG. 11 is a flowchart illustrating a process 180 that medical device system 2 may implement to detect a sleep apnea episode for patient 4 based on cardiac cycle length metrics detected by sensing circuitry of IMD 10. Process 180 may begin when the sensing circuitry of IMD 10 senses a cardiac electrogram signal exhibited by heart 6 (182). In turn, processing circuitry of medical device system 2, e.g., processing circuitry of IMD 10 used as the example hereafter, may determine a series of RRI metrics from the cardiac electrogram signal detected by the sensing circuitry of IMD 10 (184). The processing circuitry of IMD 10 may pair the RRI metrics using a consistent separation factor (186). As discussed above, an example of the consistent separation factor may be one (1), in cases of the processing circuitry of IMD 10 pairing consecutive RRI metrics. Another example of the consistent separation factor may be ten (10), in cases of the processing circuitry of IMD 10 pairing RRI metrics that are separated by ten (10) instances of measurement reads.

In turn, the processing circuitry of IMD 10 may construct a distribution of the RRI metric pairs (188). In one example, the processing circuitry of IMD 10 may use pairs of RRI metrics that are spaced by a separation factor of ten (10) to construct the distribution. For instance, the processing circuitry of IMD 10 may construct the distribution by plotting the differences between the values of the RRI metric pairs.

Additionally, the processing circuitry of IMD 10 may determine whether the constructed distribution indicates a sleep apnea episode of patient 4 (decision block 190). For instance, the processing circuitry of IMD 10 may determine whether certain characteristics of the distribution, such as a degree of dispersion (also referred to herein as "dispersedness" or "directional scatter"), match or fall within a threshold difference from a pattern associated with an episode of sleep apnea. If the processing circuitry of IMD 10 determines that the analyzed characteristics of the constructed distribution do not indicate a sleep apnea episode (NO branch of decision block 190), then the processing circuitry of IMD 10 may cause the sensing circuitry of IMD 10 to continue sensing the cardiac electrogram signal from heart 6B of patient 4 (effectively returning to block 182). However, if the processing circuitry of IMD 10 determines that the analyzed characteristics of the distribution do indicate an ongoing episode of sleep apnea (YES branch of decision block 190), then the processing circuitry of IMD 10 may transmit an indication of the detected sleep apnea episode (192). For instance, the processing circuitry of IMD 10 may control communication circuitry of IMD 10 to transmit the indication of the detected sleep apnea episode to a communication interface of external device 30B.

Figure 12:
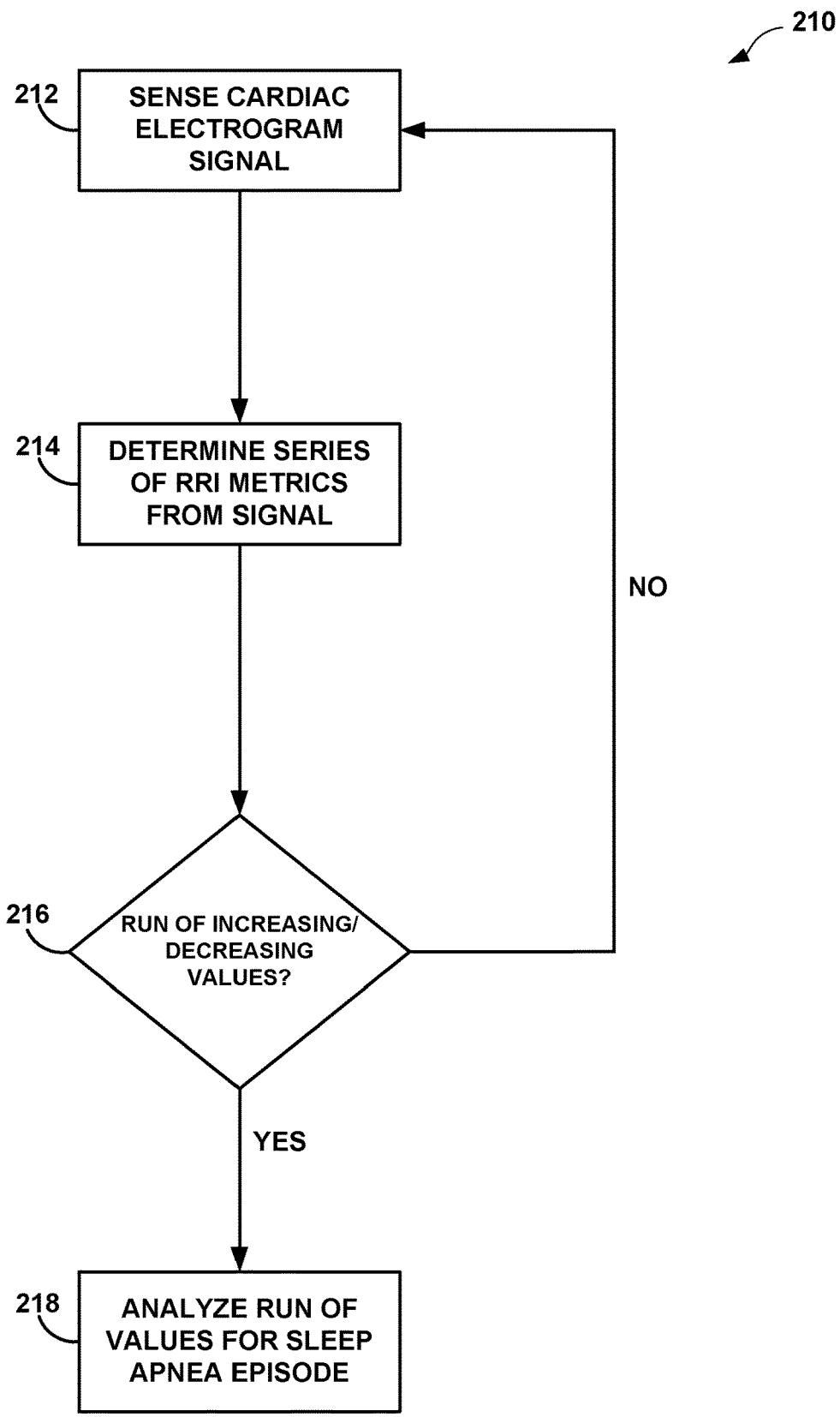
FIG. 12 is a flowchart illustrating an example process that a medical device system configured according to aspects of this disclosure may implement to detect a sleep apnea episode for a patient based on spotting one or more trends in cardiac cycle length metrics of the patient.

FIG. 12 is a flowchart illustrating a process 210 that medical device system 2 may implement to detect a sleep apnea episode for patient 4 based on spotting one or more trends in cardiac cycle length metrics detected by sensing circuitry of IMD 10. Process 210 may begin when the sensing circuitry of IMD 10 senses a cardiac electrogram signal exhibited by heart 6 (212). In turn, processing circuitry of medical device system 2, e.g., processing circuitry of IMD 10, used as the example hereafter, may determine a series of RRI metrics from the cardiac electrogram signal detected by the sensing circuitry of IMD 10 (214).

In turn, the processing circuitry of IMD 10 may determine whether the series of metrics includes a run of increasing or decreasing delta RRI amounts (decision block 216). It will be appreciated that a "run" need not be consecutive for purposes of the trend-spotting implementation of process 210, but rather, may satisfy a certain ratio within a consecutive series. For instance, the processing circuitry of IMD 10 may detect a run of increasing values if five out of seven consecutive readings shows an increase over its respective reference point. If the processing circuitry of IMD 10 does not detect a run of increasing or decreasing values (NO branch of decision block 216), then the processing circuitry of IMD 10 may cause the sensing circuitry of IMD 10 to continue sensing the cardiac electrogram signal from heart 6 of patient 4 (effectively returning to block 212). However, if the processing circuitry of IMD 10 detects a run of increasing or decreasing values (YES branch of decision block 216), then the processing circuitry of medical device system 18 may analyze the run of values to determine whether the run of values indicates an ongoing sleep apnea episode of patient 4 (218).

Figure 13:
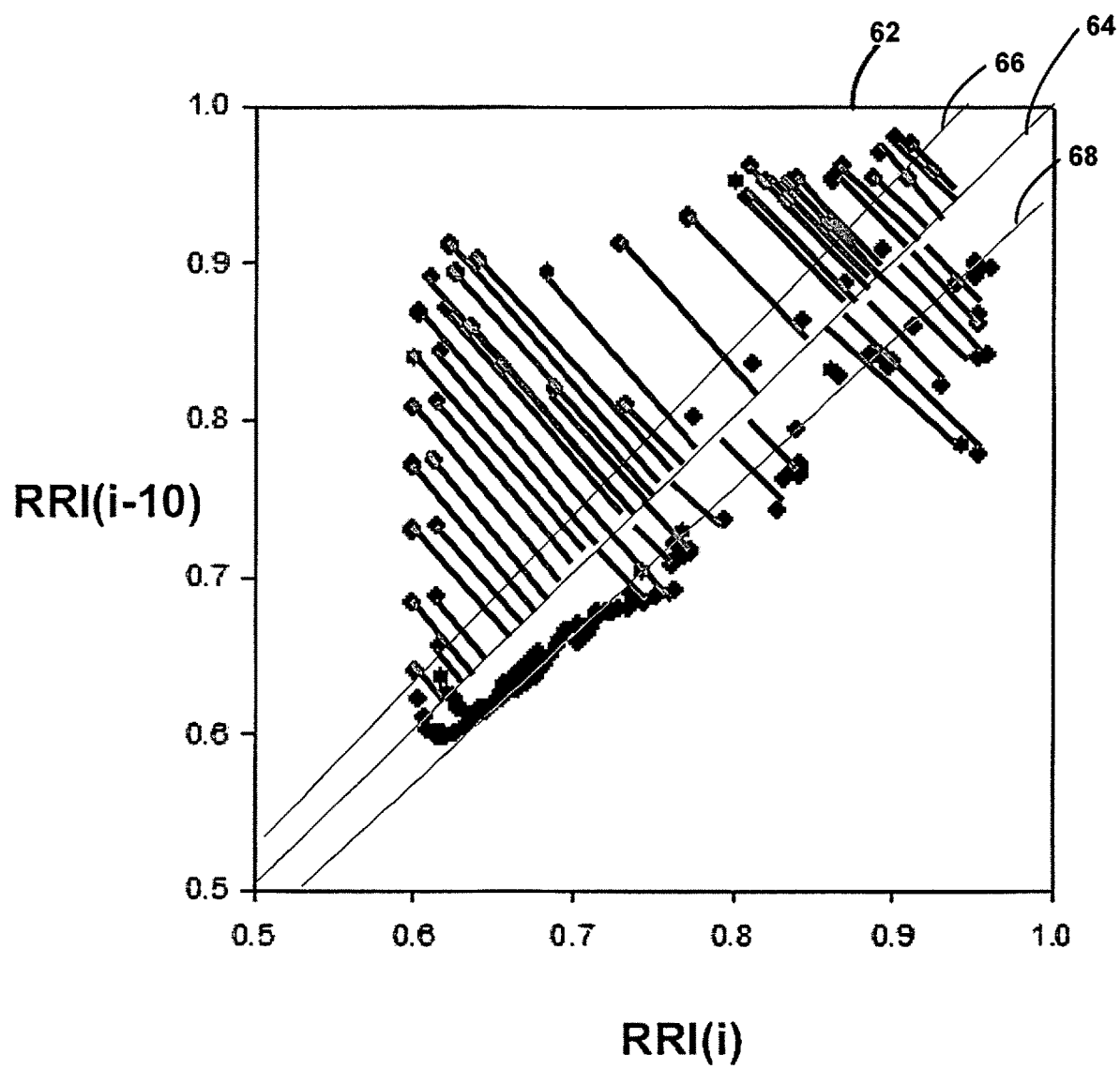
FIG. 13 illustrates the data plots of the Lorenz plot of FIG. 7 with respect to a unity line.

FIG. 13 illustrates Lorenz plot 62, which shows the data plots of Lorenz plot 60 of FIG. 7 with respect to a unity line. More specifically, Lorenz plot 62 illustrates a positive loop area, which represents an upper segment positioned above unity line 64, and a negative loop area, which represents a lower segment positioned below unity line 64. The area between band markers 66 and 68 represents a "normal band" with respect to the degree of dispersion of plot points from unity line 64. Lorenz plot 62 also shows the respective distance between the unity line and each plot point that is positioned outside the normal band (whether in the upper segment or lower segment). The numbers of plot points within the positive loop area, negative loop area, or normal band, or outside these areas or band, or ratios between the numbers of points within or outside these areas or bands, may be measures of dispersion used to detect a sleep apnea episode. The distances, e.g., means, medians, maximums, ranges, or other measures of the distances, of plot points from the unity line may also be measures of dispersion used to detect a sleep apnea episode.

Figure 14:
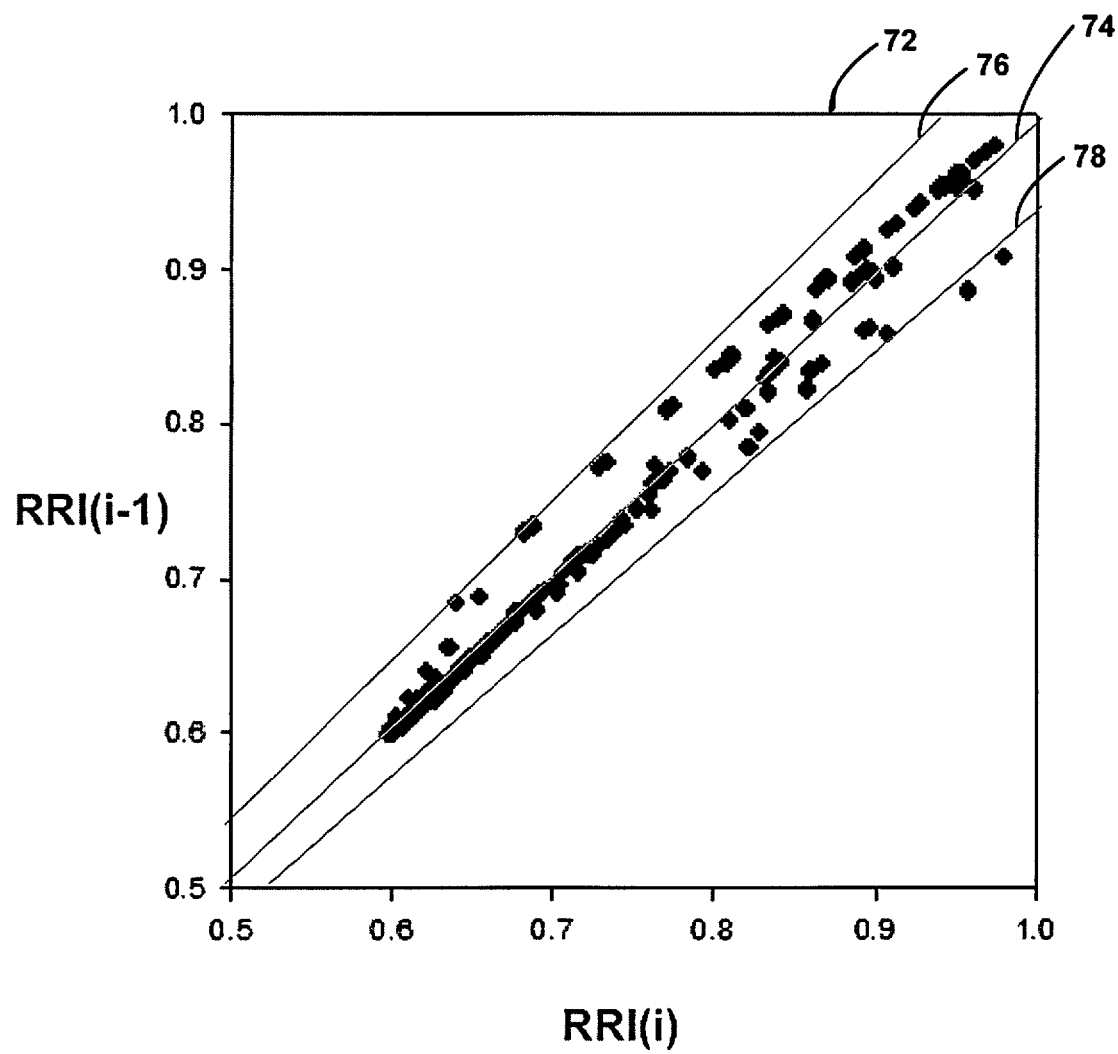
FIG. 14 illustrates the data plots of the Lorenz plot 70 of FIG. 8 with respect to a unity line.

FIG. 14 illustrates Lorenz plot 72, which shows the data plots of Lorenz plot 70 of FIG. 8 with respect to a unity line. More specifically, Lorenz plot 72 illustrates a positive loop area, which represents an upper segment positioned above unity line 74, and a negative loop area, which represents a lower segment positioned below unity line 74. The area between band markers 76 and 78 represents a "normal band" with respect to the degree of dispersion of plot points from unity line 74. Lorenz plot 72 also shows the respective distance between the unity line and each plot point that is positioned outside the normal band (whether in the upper segment or lower segment). Again, the numbers of plot points within the positive loop area, negative loop area, or normal band, or outside these areas or band, or ratios between the numbers of points within or outside these areas or bands, may be measures of dispersion used to detect a sleep apnea episode. The distances, e.g., means, medians, maximums, ranges, or other measures of the distances, of plot points from the unity line may also be measures of dispersion used to detect a sleep apnea episode.

Figure 15:
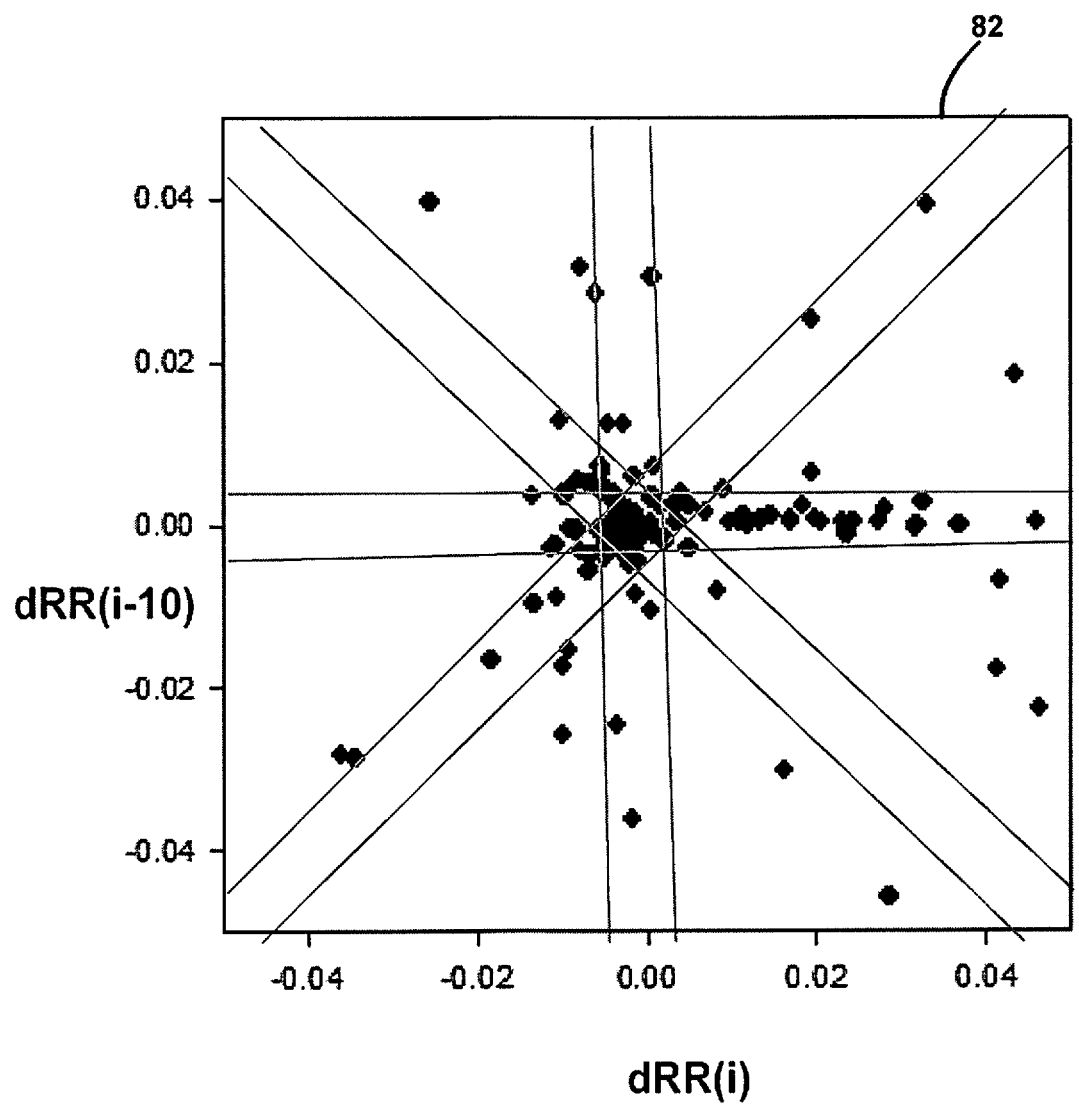
FIG. 15 shows the data plots of the Lorenz plot of FIG. 9 arranged in segments.

FIG. 15 illustrates Lorenz plot 82, which shows the data plots of Lorenz plot 80 of FIG. 9 arranged in segments. Lorenz plot 82 illustrates an example of "binning" that the processing circuitry of medical device system 18 may perform to determine degrees of dispersion or directional scatter of the dRRI points. For instance, the processing circuitry of medical device system 18 may analyze points in different segments of Lorenz plot 82 to distinguish between different states of compensation (e.g., as may occur in response to the oxygenation anomalies of a sleep apnea episode). In the example of Lorenz plot 82, the horizontal segment exhibits some degree of anisotropy (e.g., directional dependency that implies different properties in different directions).

Figure 16:
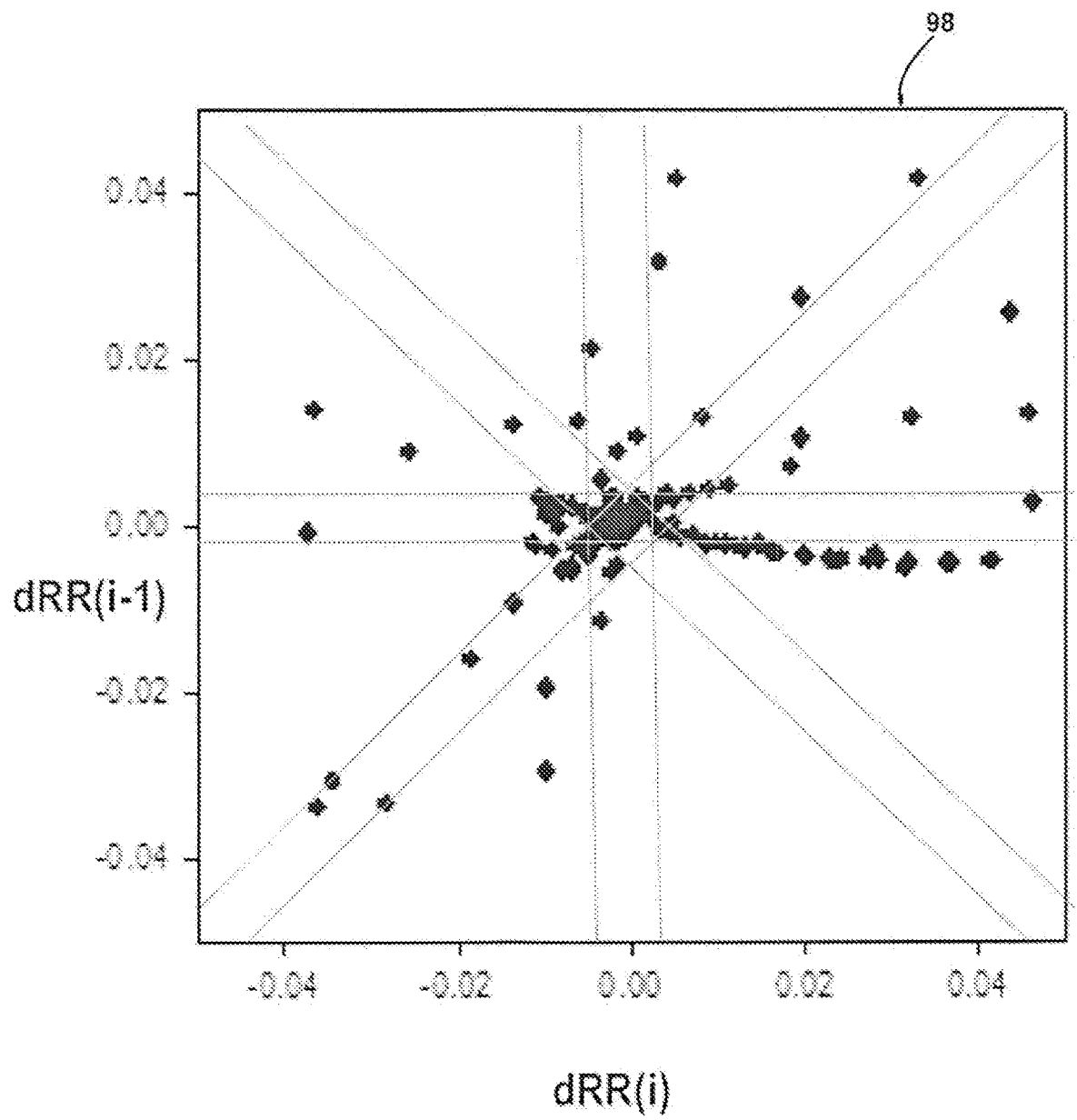
FIG. 16 shows the data plots of Lorenz plot of FIG. 10 arranged in segments.

FIG. 16 illustrates Lorenz plot 98, which shows the data plots of Lorenz plot 96 of FIG. 10 arranged in segments. Lorenz plot 98 illustrates an example of "binning" that the processing circuitry of medical device system 18 may perform to determine degrees of dispersion or directional scatter of the dRRI points. For instance, the processing circuitry of medical device system 18 may analyze points in different segments of Lorenz plot 98 to distinguish between different states of compensation (e.g., as may occur in response to the oxygenation anomalies of a sleep apnea episode). In the example of Lorenz plot 98, the off-diagonal/horizontal segment exhibits some degree of anisotropy (e.g., directional dependency that implies different properties in different directions).

As used herein, an implantable medical device (IMD) may include, be, or be part of a variety of devices or integrated systems, such as, but not limited to, implantable cardiac monitors (ICMs), implantable pacemakers, including those that deliver cardiac resynchronization therapy (CRT), implantable cardioverter defibrillators (ICDs), diagnostics device, cardiac device, etc. Various examples have been described that include detecting episodes of sleep apnea using cardiac cycle length metrics. In addition, pulmonary therapy may be provided to mitigate the severity of the sleep apnea episode or counter the effects of the sleep apnea episode. Any combination of detection and therapy for sleep apnea episodes is contemplated. These and other examples are within the scope of the following claims.

What is claimed is:

1. An implantable medical device (IMD) system comprising:
   communication circuitry configured to communicate with an external computing device;
   sensing circuitry configured to sense a cardiac signal that varies as a function of a cardiac cycle of a patient; and
   processing circuitry configured to:
      determine a series of consecutive cardiac cycle length metric values based on the sensed cardiac signal;
      identify a plurality of pairs of the cardiac cycle length metrics, each of the pairs of cardiac cycle length metrics separated by an integer 'n' of the cardiac cycle length metrics;
      construct a distribution of the pairs of cardiac cycle length metrics based on values of the cardiac cycle length metrics for each of the pairs;
      detect a sleep apnea episode of the patient based on dispersion information of the constructed distribution; and
      transmit, via the communication circuitry, an indication of the detected sleep apnea episode to the external computing device.

2. The IMD system of claim 1, wherein the processing circuitry is further configured to determine the dispersion information based on one or more clustering characteristics associated with the constructed distribution.

3. The IMD of claim 2, wherein the processing circuitry is configured to:
   compare the clustering characteristics to a threshold; and
   detect the sleep apnea condition based on the comparison.

4. The IMD of claim 2, wherein the processing circuitry is configured to transmit, via the communication circuitry, a communication to trigger deliver therapy to the patient to remediate one or more effects of the detected sleep apnea event.

5. The IMD of claim 4, wherein the therapy comprises one or more of a continuous positive airway pressure (CPAP) therapy, a bilevel positive airway pressure (BiPAP) therapy, or a cardiac pacing therapy.

6. The IMD system of claim 1, wherein each cardiac cycle length metric value of the series of consecutive cardiac cycle length metric values comprises a value of one of a series of consecutive cardiac cycle lengths.

7. The IMD system of claim 1, wherein each cardiac cycle length metric value of the series of consecutive cardiac cycle length metric values comprises a difference between values of two consecutive cardiac cycle lengths of a series of consecutive cardiac cycle lengths.

8. The IMD system of claim 1, wherein the processing circuitry is configured to detect the sleep apnea episode based on the dispersion information indicating a degree of dispersion above a threshold level of dispersion.

9. The IMD system of claim 1, wherein the degree of dispersion comprises a degree of dispersion of the plurality of pairs from a unity line.

10. The IMD of claim 1, further comprising:
   a housing configured for subcutaneous implantation, wherein the housing houses the sensing circuitry; and
   a plurality of electrodes coupled to the housing and to the sensing circuitry,
   wherein the sensing circuitry is configured to sense the cardiac signal via one or more electrodes of the plurality of electrodes.

11. A method of detecting sleep apnea by an implantable medical device (IMD) system, the method comprising:
   sensing, by sensing circuitry of the IMD system, a cardiac signal that varies as a function of a cardiac cycle of a patient;
   determining, by processing circuitry of the IMD system, a series of consecutive cardiac cycle length metric values based on the sensed cardiac signal;
   identifying, by the processing circuitry of the IMD system, a plurality of pairs of the cardiac cycle length metrics, each of the pairs of cardiac cycle length metrics separated by an integer 'n' of the cardiac cycle length metrics;
   constructing, by the processing circuitry of the IMD system, a distribution of the pairs of cardiac cycle length metrics based on values of the cardiac cycle length metrics for each of the pairs;
   detecting, by the processing circuitry of the IMD system, a sleep apnea episode of the patient based on dispersion information of the constructed distribution; and
   transmitting, by the processing circuitry of the IMD system, via communication circuitry of the IMD system, an indication of the detected sleep apnea episode to an external computing device.

12. The method of claim 11, further comprising determining, by the processing circuitry of the IMD system, the dispersion information based on one or more clustering characteristics associated with the constructed distribution.

13. The method of claim 12, further comprising:
   comparing, by the processing circuitry of the IMD system, the clustering characteristics to a threshold; and
   detecting, by the processing circuitry of the IMD system, the sleep apnea condition based on the comparison.

14. The method of claim 12, further comprising detecting, by the processing circuitry of the IMD system, the clustering characteristics at least in part by:

determining, by the processing circuitry of the IMD system, one or more bins using the plurality of pairs of the cardiac cycle length metrics; and
   determining, by the processing circuitry of the IMD system, a number of pairs in each bin of the one or more bins.

15. The method of claim 11, wherein each cardiac cycle length metric value of the series of consecutive cardiac cycle length metric values comprises a value of one of a series of consecutive cardiac cycle lengths.

16. The method of claim 11, wherein each cardiac cycle length metric value of the series of consecutive cardiac cycle length metric values comprises a difference between values of two consecutive cardiac cycle lengths of a series of consecutive cardiac cycle lengths.

17. The method of claim 11, wherein detecting the sleep apnea episode based on the determined dispersion information comprises detecting, by the processing circuitry of the IMD system, the sleep apnea episode based on the dispersion information indicating a degree of dispersion above a threshold level of dispersion.

18. The method of claim 11, wherein the degree of dispersion comprises a degree of dispersion of a plotting of the plurality of pairs from a unity line.

19. An implantable medical device (IMD) system comprising:
   means for sensing a cardiac signal that varies as a function of a cardiac cycle of a patient;
   means for determining a series of consecutive cardiac cycle length metric values based on the sensed cardiac signal;
   means for identifying a plurality of pairs of the cardiac cycle length metrics, each of the pairs of cardiac cycle length metrics separated by an integer 'n' of the cardiac cycle length metrics;
   means for constructing a distribution of the pairs of cardiac cycle length metrics based on values of the cardiac cycle length metrics for each of the pairs; and
   means for detecting a sleep apnea episode of the patient based on dispersion information of the constructed distribution;
   means for generating an indication of the detected sleep apnea episode; and
   means for transmitting the indication of the detected sleep apnea episode to an external computing device.

20. A non-transitory computer-readable storage medium encoded with instructions that, when executed, cause processing circuitry of an implantable medical device (IMD) system to:
   sense a cardiac signal that varies as a function of a cardiac cycle of a patient;
   determine a series of consecutive cardiac cycle length metric values based on the sensed cardiac signal;
   identify a plurality of pairs of the cardiac cycle length metrics, each of the pairs of cardiac cycle length metrics separated by an integer 'n' of the cardiac cycle length metrics;
   construct a distribution of the pairs of cardiac cycle length metrics based on values of the cardiac cycle length metrics for each of the pairs; and
   detect a sleep apnea episode of the patient based on dispersion information of the constructed distribution; and
   generate an indication of the detected sleep apnea episode; and transmit the indication of the detected sleep apnea episode to an external computing device.

* * * * *